(12) United States Patent
Houchen et al.

(10) Patent No.: US 7,956,044 B1
(45) Date of Patent: Jun. 7, 2011

(54) COMPOSITIONS COMPRISING INHIBITORS OF RNA BINDING PROTEINS AND METHODS OF PRODUCING AND USING SAME

(75) Inventors: Courtney Houchen, Edmond, OK (US); Shrikant Anant, Edmond, OK (US); Sripathi M. Sureban, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 12/384,387

(22) Filed: Apr. 3, 2009

Related U.S. Application Data

(60) Provisional application No. 61/123,045, filed on Apr. 3, 2008.

(51) Int. Cl.
*A01N 43/04* (2006.01)
*A61K 31/70* (2006.01)
*C07H 21/02* (2006.01)
*C07H 21/04* (2006.01)

(52) U.S. Cl. ..... 514/44; 536/23.1; 536/24.3; 536/24.33; 536/24.5

(58) Field of Classification Search .................. 536/23.1, 536/24.3, 24.33, 24.5; 514/44
See application file for complete search history.

(56) References Cited

U.S. PATENT DOCUMENTS

| 7,345,027 B2 | 3/2008 | Tolentino et al. |
| 7,511,025 B2 | 3/2009 | Wyatt et al. |
| 7,511,132 B2 | 3/2009 | Khvorova et al. |

OTHER PUBLICATIONS

Battelli et al. (Mol. Cell. Neurosci., 2006 vol. 31:85-96).*
Elbashir et al. (Methods, 2002 vol. 26:199-213).*
Ratti et al. (Journal of Cell Science, 2006 vol. 119:1442-1452).*
May, et al, "DCAMKL-1 and LGR5 Mark Quiescent and Cycling Intestinal Stem Cells Respectively", Stem Cell, pp. 1-38 (2009).
Sureban et al., "Knockdown of RNA Binding Portein Musashi-1 Leads to Tumor Regression In Vivo", Gastroenterology 134:1448-1458, (2008).

* cited by examiner

*Primary Examiner* — Sean McGarry
*Assistant Examiner* — Terra Cotta Gibbs
(74) *Attorney, Agent, or Firm* — Dunlap Codding, P.C.

(57) ABSTRACT

Compositions for inhibiting RNA binding proteins, as well as methods of producing and using same, are disclosed herein.

Figure 1:
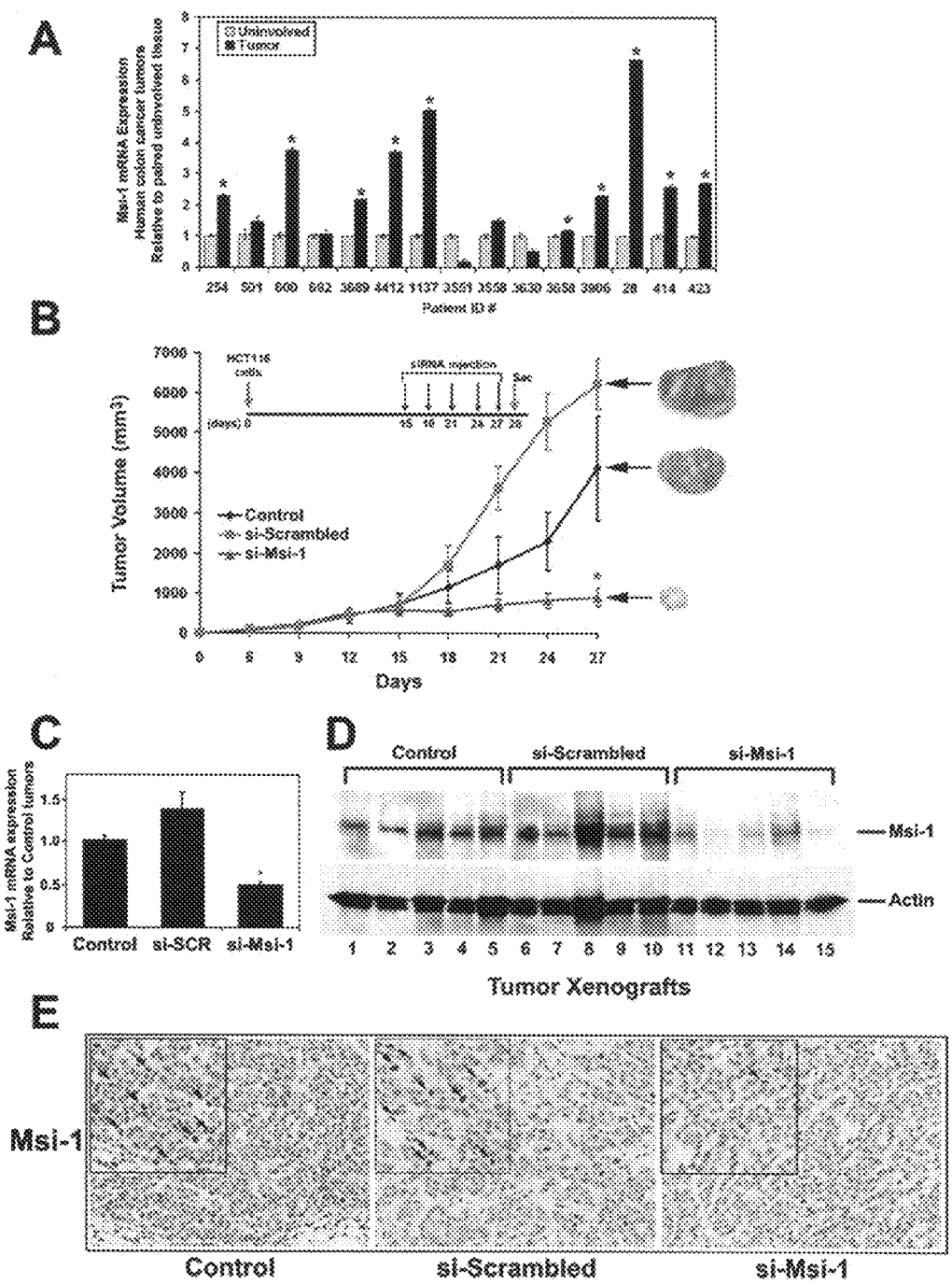

11 Claims, 13 Drawing Sheets
(11 of 13 Drawing Sheet(s) Filed in Color)

Figure 2
A
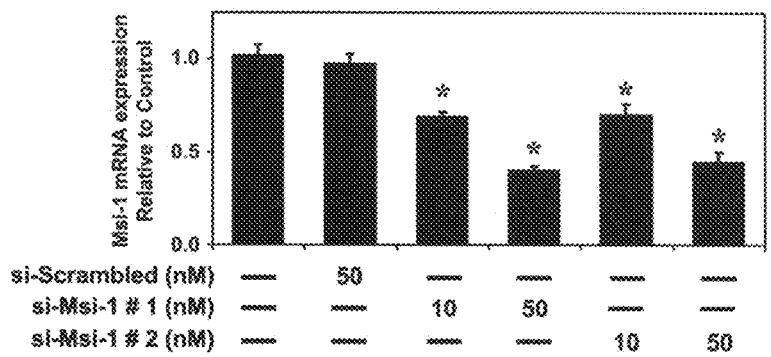
B
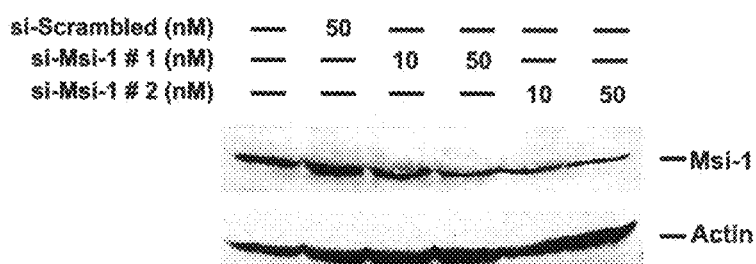
C
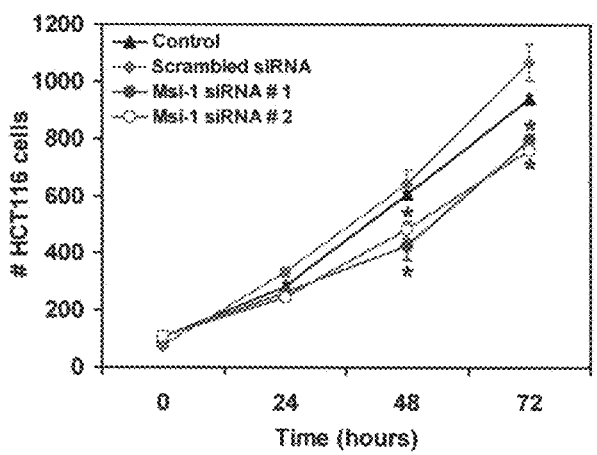
D
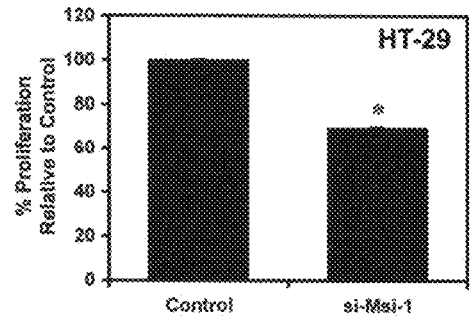

Figure 7
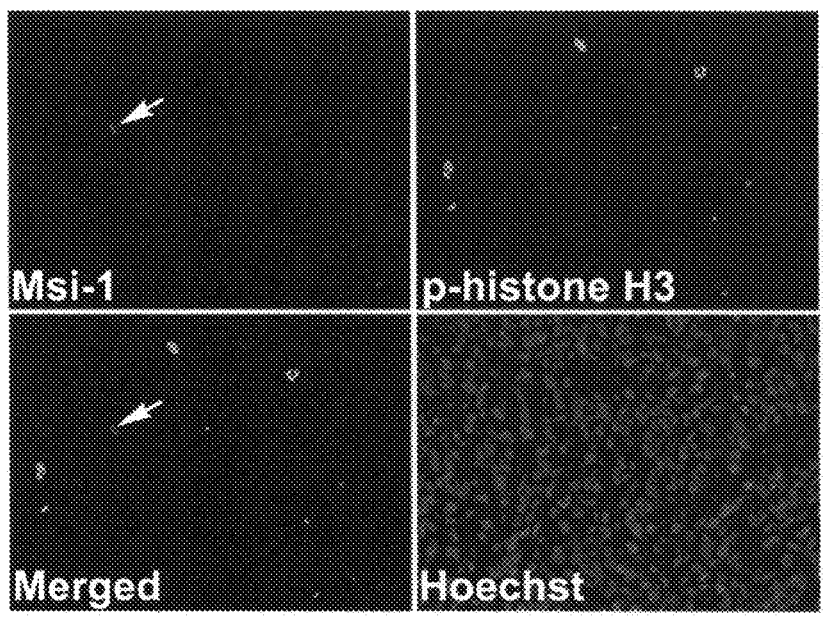
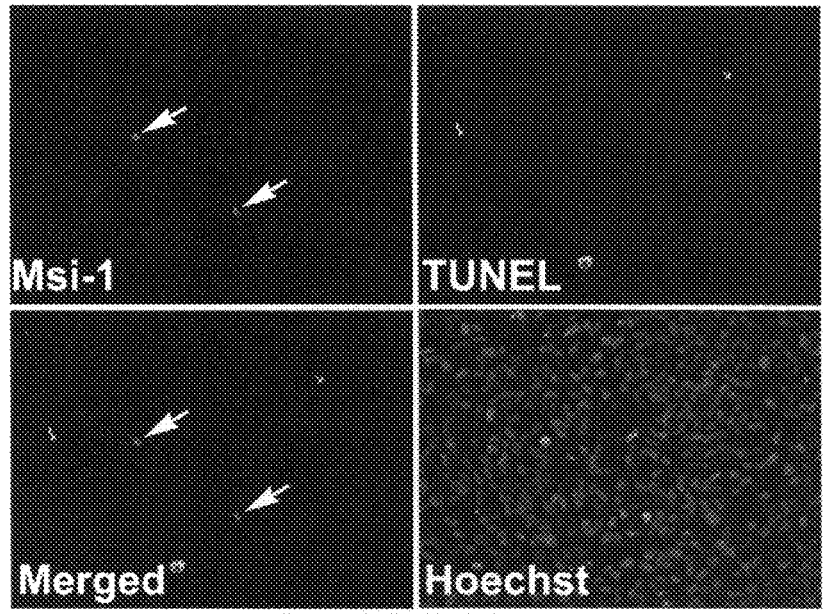

Figure 8
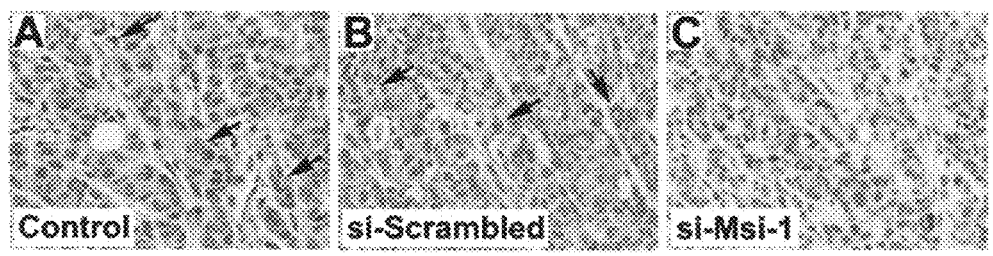
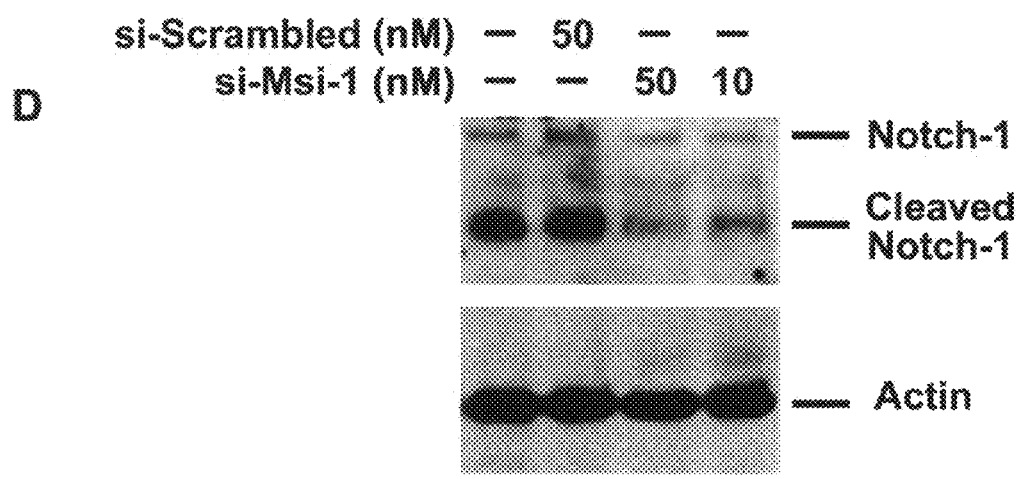
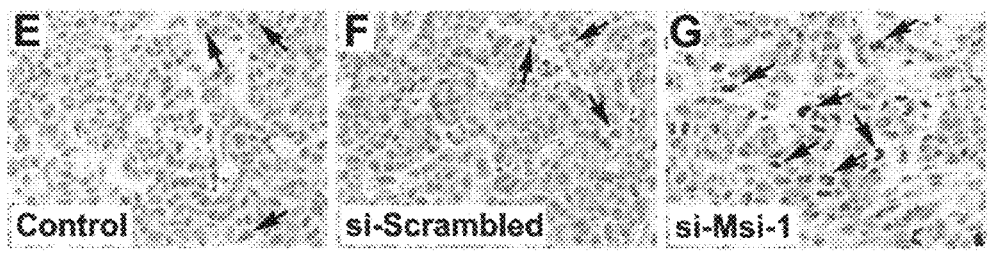
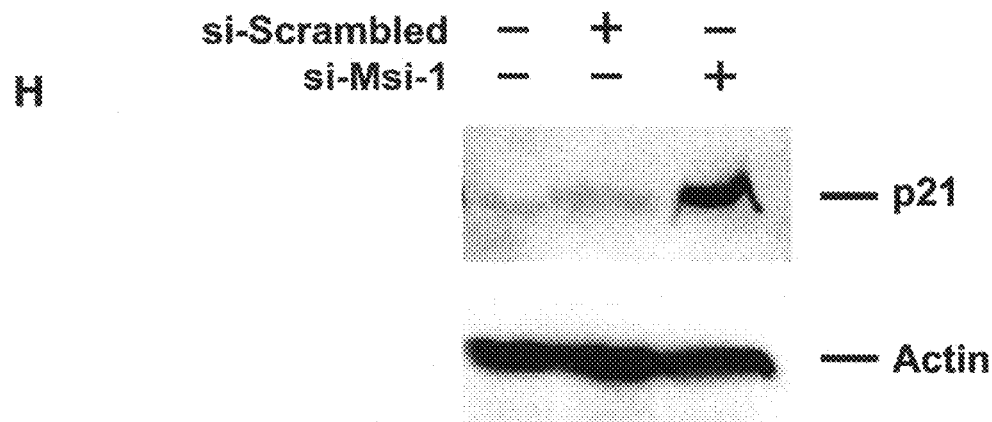

SEQUENCE LISTING

<160> NUMBER OF SEQ ID NOS: 9

<210> SEQ ID NO 1
<211> LENGTH: 2950
<212> TYPE: RNA

<213> ORGANISM: Homo sapiens

<400> SEQUENCE: 1

| | | | | | |
|---|---|---|---|---|---|
| gcgccgagcg | ccgccgccgc | cgccgccgcc | gccgcuccgc | ugcccgcgcc | gccgcggcu     60 |
| cccgauggag | acugacgcgc | cccagcccgg | ccucgccucc | ccggacucgc | cgcacgaccc   120 |
| cugcaagaug | uucaucgggg | gacucaguug | gcagacuacg | caggaagggc | ugcgcgaaua   180 |
| cuucggccag | uucggggagg | ugaaggagug | ucuggugaug | cgggacccccc | ugaccaagag   240 |
| auccaggggu | uucggcuucg | ucacuuucau | ggaccaggcg | ggguggaaua | aagugcuggc   300 |
| gcaaucgcgg | cacgagcucg | acuccaaaac | aauugacccu | aagguggccu | ucccucggcg   360 |
| agcacagccc | aagaugguga | cucgaacgaa | gaagaucuuu | guggggggc | ugucggugaa   420 |
| caccacggug | gaggacguga | agcaauauuu | ugagcaguuu | gggaaggugg | acgacgccau   480 |
| gcugauguuu | gacaaaaacca | ccaaccggca | ccgaggguuc | ggguuuguca | cguuugagag   540 |
| ugaggacauc | guggagaaag | ugugugaaau | ucauuuucau | gaaaucaaca | acaaaauggu   600 |
| ggaauguaag | aaagcucagc | caaaggaggu | gaugucgcca | acgggcucag | cccgggggag   660 |
| gucucgaguc | augcccuacg | gaauggacgc | cuucaugcug | ggcaucggca | ugcugggguua  720 |
| cccagguuuc | caagccacaa | ccuacgccag | ccggaguuau | acaggccucg | ccccuggcua   780 |
| caccuaccag | uucccgaaau | uccguguaga | gcggacccccu | cucccgagcg | ccccagcccu   840 |
| ccccgagcuu | acagccauuc | cucucacugc | cuacggacca | augccggcgg | cagcggcggc   900 |
| agcggcugug | guucgaggga | caggcucuca | ccccuggacg | auggcucccc | cuccagguuc   960 |
| gacucccagc | cgcacagggg | gcuuccuggg | gaccaccagc | cccggcccca | uggccgagcu  1020 |
| cuacggggcg | gccaaccagg | acucgggggu | cagcaguuac | aucagcgccg | ccagcccugc  1080 |
| ccccagcacc | ggcuucggcc | acagucuugg | gggcccuuug | auugccacag | ccuucaccaa  1140 |
| uggguaccac | ugaagcaggg | gacgguggca | ggagcgcccc | agccugcagc | ugacugagga  1200 |
| ccacgaguga | gccagcgagg | gggcgggaga | ccucagccgc | agccgccgcc | cccuccccug  1260 |
| cagcgacucg | gacccgcuac | ugccugcccc | caacuccccg | ggcccggccc | cugcccugcu  1320 |
| gccccccaaca | gcgucuggcu | ccccuacuaa | cgucccccuc | uucgcccuug | ccccauccc   1380 |
| cacccgcccc | ucuccggcc | cugcuuuuau | uuauuuugga | uuagccgguu | gccaccccca  1440 |
| gcccucuggu | ccaucccucc | cuccgugccg | cgccccccua | ggaccgcccc | cuccccaaaa  1500 |
| ggcuuuugga | uuugugcaua | gcuggaguga | aggcggaggg | agccugcuac | aggccgcagc  1560 |
| ccaaccccug | uuuuuuauuc | agauuucccc | uccuuuaccc | uuuccuuuu | uuuuuuuuu   1620 |
| uuuuuuuua | aagaaaccuu | uuuuaaacua | uuucagguu | ugugaaugug | aagccccagg  1680 |
| ccgcagggg | caaggggcca | ggugccccccc | accagcugag | aacaaagugu | cuaucugggu  1740 |
| gugggcccccu | ggccgccucc | cuccagcccu | ggagaggagg | gcagggcugc | ggggaggcca  1800 |
| ggccgagccc | cuggaaccau | cccgucccugu | aucauaugua | aauacuguga | ggugaugugc  1860 |
| ccaccccucu | cuaagacccc | ucggggguga | ggggcucccc | ccuccccugu | uucuguccccc 1920 |
| ucagacaccg | uuacuguaag | cuugcaggcc | ucagcgugg | ccacgcagg | cccgcucucu  1980 |
| caggcccuca | gggucaaggc | cuugguugga | ccugcccacu | ccaaaaaccc | agugugggg   2040 |
| caaagggcgu | gggaagagca | gggcuugccc | agcgacacug | cuggacagga | auuaacucuc  2100 |
| caaaggucuc | cccugcuccc | uaccuagguu | ggggcuucau | gguucugcu | cagucuguccc 2160 |
| cccuuccccc | ucgaccccccg | caaugagugg | gcaccagggg | acgcucuggc | gagggcagac  2220 |
| cccaggggaa | agcaaagggc | gucucaggga | accccccacau | ucucucacug | aaguuuccca  2280 |

-continued

| | |
|---|---|
| ccaggaugac cccacagcca gagucccuug gcagccccuc accccagacc ccccuucuaa | 2340 |
| ggaaaaagag agguucagag cguuggaccu ucaugaacag uggccuggcu ggcguggcag | 2400 |
| ggccaaggcc cacccacugc caucccccuu cuguguguc cucucccca guuaugaggc | 2460 |
| ccagggccug agcucucuuc cccagcauug ccccacccg gaaacccac cuuuggagag | 2520 |
| uuaauugucu gugugaggug cuuaaccuau cagcccugag aacacaaagc aauaaucuuu | 2580 |
| guuacugaga ugcgcggcug uucguguuu ggguuuuuu uuuuuuaau guuuccuaau | 2640 |
| aaagagaag cugcauuuua uugguuuuua uuuuaauuu ucuacacguu ugagcugagu | 2700 |
| ccugagacac uuagcuuccc ucuccccau ucccggaccc uuccacccca cugggcccaa | 2760 |
| ccaugggcuc aggacccugg aauuccguuu ucugauuugc uuuggauuu uuuuuuuu | 2820 |
| uaagauguua caugguguuu cgaagccagc aaguuaccau ccuccggugu cucuucucuc | 2880 |
| cacaucugua acuucuuuuu ccagguuuua uuuucaguuu uaaauuccua auaaauuauu | 2940 |
| ugaaaacguu | 2950 |

```
<210> SEQ ID NO 2
<211> LENGTH: 17
<212> TYPE: RNA
<213> ORGANISM: Homo sapiens

<400> SEQUENCE: 2
```

| | |
|---|---|
| cuuuuggauu ugugcau | 17 |

```
<210> SEQ ID NO 3
<211> LENGTH: 17
<212> TYPE: RNA
<213> ORGANISM: Homo sapiens

<400> SEQUENCE: 3
```

| | |
|---|---|
| acaucgugga gaaagug | 17 |

```
<210> SEQ ID NO 4
<211> LENGTH: 21
<212> TYPE: DNA
<213> ORGANISM: Homo sapiens

<400> SEQUENCE: 4
```

| | |
|---|---|
| ggtgatccac atctgctgga a | 21 |

```
<210> SEQ ID NO 5
<211> LENGTH: 20
<212> TYPE: DNA
<213> ORGANISM: Homo sapiens

<400> SEQUENCE: 5
```

| | |
|---|---|
| atcattgctc ctcctcaggg | 20 |

```
<210> SEQ ID NO 6
<211> LENGTH: 24
<212> TYPE: DNA
<213> ORGANISM: Homo sapiens

<400> SEQUENCE: 6
```

| | |
|---|---|
| cagtttcgga cctatctctg aggt | 24 |

```
<210> SEQ ID NO 7
<211> LENGTH: 23
<212> TYPE: DNA
<213> ORGANISM: Homo sapiens
```

```
<400> SEQUENCE: 7
aaggtgatga aaccaaaacc cct                                            23

<210> SEQ ID NO 8
<211> LENGTH: 20
<212> TYPE: DNA
<213> ORGANISM: Homo sapiens

<400> SEQUENCE: 8
tgagctggca gacctcacca                                                20

<210> SEQ ID NO 9
<211> LENGTH: 20
<212> TYPE: DNA
<213> ORGANISM: Homo sapiens

<400> SEQUENCE: 9
aaaccgaagc ctctggagcg                                                20
```

US 7,956,044 B1

COMPOSITIONS COMPRISING INHIBITORS OF RNA BINDING PROTEINS AND METHODS OF PRODUCING AND USING SAME

CROSS REFERENCE TO RELATED APPLICATIONS

This application claims benefit under 35 U.S.C. 119(e) of provisional application U.S. Ser. No. 61/123,045, filed Apr. 3, 2008; the entire contents of which is hereby expressly incorporated herein by reference.

STATEMENT REGARDING FEDERALLY SPONSORED RESEARCH OR DEVELOPMENT

Some aspects of this invention were made in the course of Grants R-01 DK-066161 and R-01 DK-002822 awarded by the National Institutes of Health, and therefore the Government has certain rights in some aspects of this invention.

BACKGROUND OF THE INVENTION

1. Field of the Invention

The presently disclosed and claimed invention relates generally to anti-cancer compositions and methods of producing and using same, and in particular, but not by way of limitation, to compositions comprising inhibitors of RNA binding proteins and methods of producing and using same.

2. Description of the Background Art

Stem cells are ultimately responsible for the entire cell production process in a particular tissue. They have a potential capability of large numbers of cell division and maintenance of cell replacement during the entire life of an animal (Potten et al., 2003). The epithelial cells of intestinal villi of the small intestinal mucosa are replaced within 2-3 days, and this rapid cell turnover, in addition to self-renewal by the intestinal tissue, is governed by epithelial stem cells present in the crypts of the small intestine (Okano et al., 2005). The Musashi-1 (Msi-1) gene encodes an RNA binding protein involved in early asymmetric divisions generating differentiated cells from neural stem cells or progenitor cells. Msi-1 expression was observed in the small intestine at the fourth-sixth cell position from the bottom of the crypts and in the cells in the deepest portion of the large intestine, where the possibility of stem cells is considered to be high (Okano et al., 2005; and Marshman et al., 2002).

Several lines of evidence suggest that some tumor types are maintained by a small population of self-renewing cells or "cancer stem cells". The transformation of a normal mucosal epithelial cell to an invasive colorectal carcinoma occurs via a well-coordinated accumulation of mutations in a series of critical genes (Riehl et al., 2006). In gut, tumorigenesis arises from the stem cell population located near the base of intestine and colonic crypts (Potten et al., 2003). Msi-1 has been shown to be a positive regulator of Notch signaling through its interaction and translational repression of mammalian Numb (mNumb) messenger RNA (mRNA) (an inhibitor of Notch signaling) (Okano et al., 2002). Recently, reports have emerged showing that Msi-1 regulates neuronal development through the translational repression of p21$^{WAF1/Cip1}$ (Battelli et al., 2006; Sakakibara et al., 1996; and Imai et al., 2001). Msi-1 expression in intestinal tumors of APC$^{min/+}$ mice is thought to be caused by activation of Notch signaling. However, the definitive role of Msi-1 in colon cancer and cancer progression is currently unclear.

Therefore, there is a need in the art for new and improved methods of preventing tumor growth by targeting cancer stem cells. It is to said methods of preventing tumor growth, as well as compositions utilized in said methods, as well as methods of producing the compositions, that the presently disclosed and claimed invention is directed.

BRIEF DESCRIPTIONS OF THE DRAWINGS

This patent or application file contains at least one drawing executed in color. Copies of this patent or patent application publication with color drawing(s) will be provided by the Office upon request and payment of the necessary fee.

FIG. 1 demonstrates that Msi-1 is required for tumorigenesis. (A) Total RNA isolated from human colorectal tumors (black bars) and paired surrounding uninvolved tissue (grey bars) was reverse transcribed and subjected to real-time RT PCR for Msi-1. Error bars represent 95% confidence interval; * p<0.01. Msi-1 expression was increased in the tumors compared to uninvolved tissues. (B) HCT116 cells ($6 \times 10^6$) were injected into nude mice to generate human colon cancer tumor xenograft, at day 15 were injected with siRNA specific for Msi-1 (si-Msi-1) or scrambled siRNA (si-scrambled) (n=5) for every 3 days as depicted in scheme (Inset figure). Length and width of palpable tumors were measured, and tumor volumes calculated at the indicated time points. Tumors excised from the mice at day 28 following 5 injections of siRNA are represented in the figure; error bars indicate SEM; asterisk p<0.05 compared to Control tumors and p<0.01 compared to scrambled siRNA treated tumors, calculated using a two-tailed student's t-test compared to control or si-scrambled treated tumors. (C) The expression of Msi-1 mRNA was demonstrated by real-time RT PCR. Shown are the levels of Msi-1 mRNA in the control, si-scrambled and si-Msi-1 treated tumors. n=5; error bars represent 95% confidence interval; * p<0.01. (D) Western blot analysis was performed on the tumors as indicated for Msi-1. n=5 of the tumors in each group. Actin was used as internal control. (E) Immunohistochemistry was performed for the tumors for Msi-1 indicated by the arrows in the inset of each tumor from each group.

FIG. 2 demonstrates that Msi-1 is essential for cell proliferation. (A) HCT116 cells transfected with 10 and 50 nM of si-Msi-1 #1, si-Msi-1 #2 or 50 nM of si-scrambled and after 48 h, RNA was isolated and subjected to real-time RT PCR for Msi-1. n=3; error bars represent 95% confidence interval; * p<0.01. (B) HCT116 cells transfected similarly for 72 h were subjected to western blot analysis for Msi-1. Shown is the representative figure of one such experiment. Actin was used as internal control. (C)HCT116 cells were transfected with 30 nM of two (#1—used in the tumor xenograft study) si-Msi-1 or si-scrambled and was subjected to hexosaminidase assay for proliferation assessment at time point indicate after 48 h after initial siRNA transfection; error bars indicate SEM; * p<0.01. (D) HT29 cells were transfected with 30 nM of si-Msi-1 #1 and proliferation was assessed at 96 h after initial siRNA transfection; error bars indicate SEM; * p<0.01.

Figure 3:
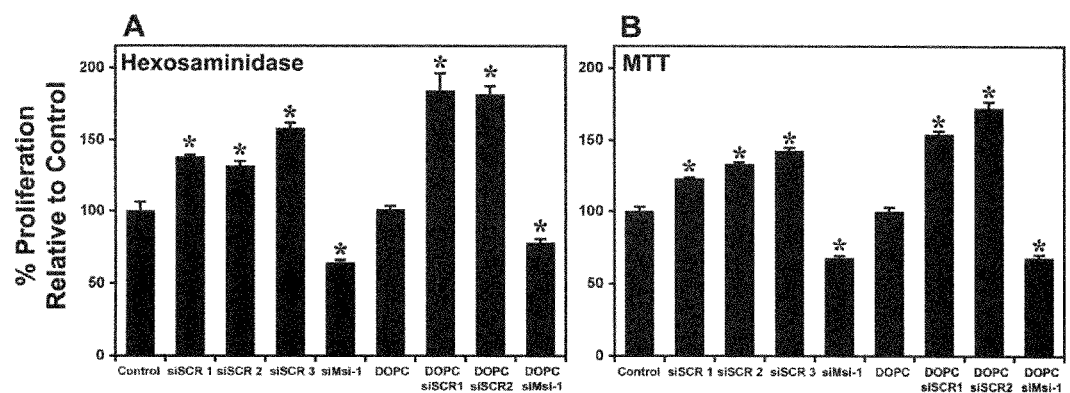

FIG. 3 demonstrates an assessment of proliferation by Hexosaminidase and MTT assays. HCT116 cells were transfected with 30 nM of si-Msi-1 or si-Scrambled as indicated using Transfectol™ transfection reagent. Scrambled and Msi-1 siRNAs were also transfected to HCT116 cells using DOPC (transfection reagent used in tumor xenografts) wherever indicated. The proliferation was assessed using hexosaminidase assay (A) and MTT assay (B). Error bars indicate SEM; * p<0.05.

Figure 4:
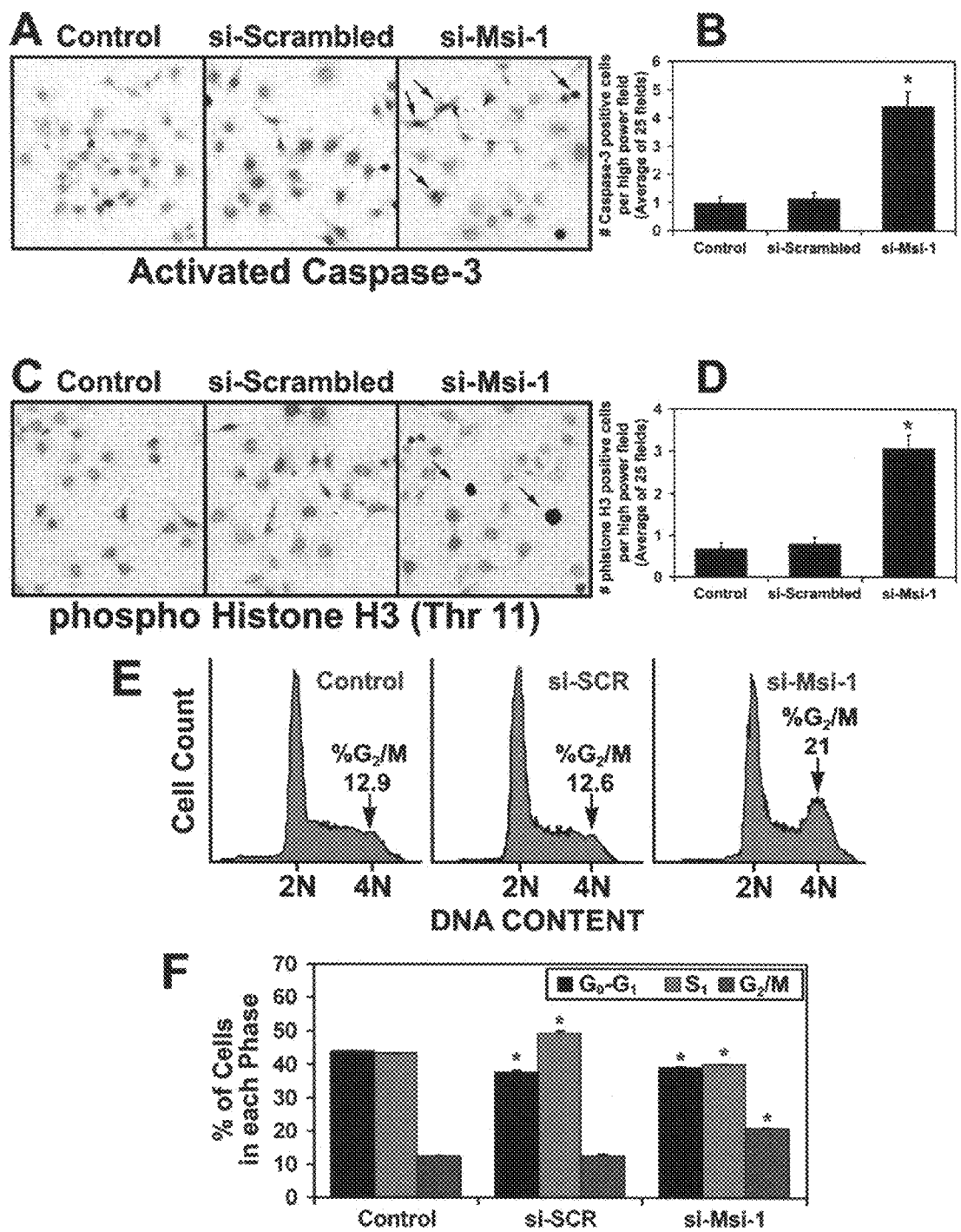

FIG. 4 demonstrates that knockdown of Msi-1 induces apoptosis and $G_2/M$ arrest. (A) HCT116 cells transfected with 30 nM si-Msi-1 #1 or si-scrambled for 48 h, fixed and immunohistochemically stained for activated caspase-3. Caspase-3 positive cells are indicated by the arrows. (B) Caspase-3 positive cells counted were plotted as an average of 25 high power fields. Error bars indicate the SEM; * p<0.01. (C) siRNA transfected cells as indicated is stained for phosphorylated histone H3 (Thr 11). Phosphorylated Histone H3 positive cells are indicated by the arrows and cells counted are plotted as a bar graph (D) as an average of 25 high power fields. Error bars indicate the SEM; * p<0.01. (E) HCT116 cells were transfected with 30 nM si-Msi-1 or si-scrambled and was subjected to FACS analysis. Representative cell cycle profile for each treatment as indicated. 2N represents $G_o$-$G_1$ phase and 4N represents $G_2/M$ phase. (F) Graphical representation of the fractions of each phase. Error bars indicate the SEM; * p<0.01.

Figure 5:
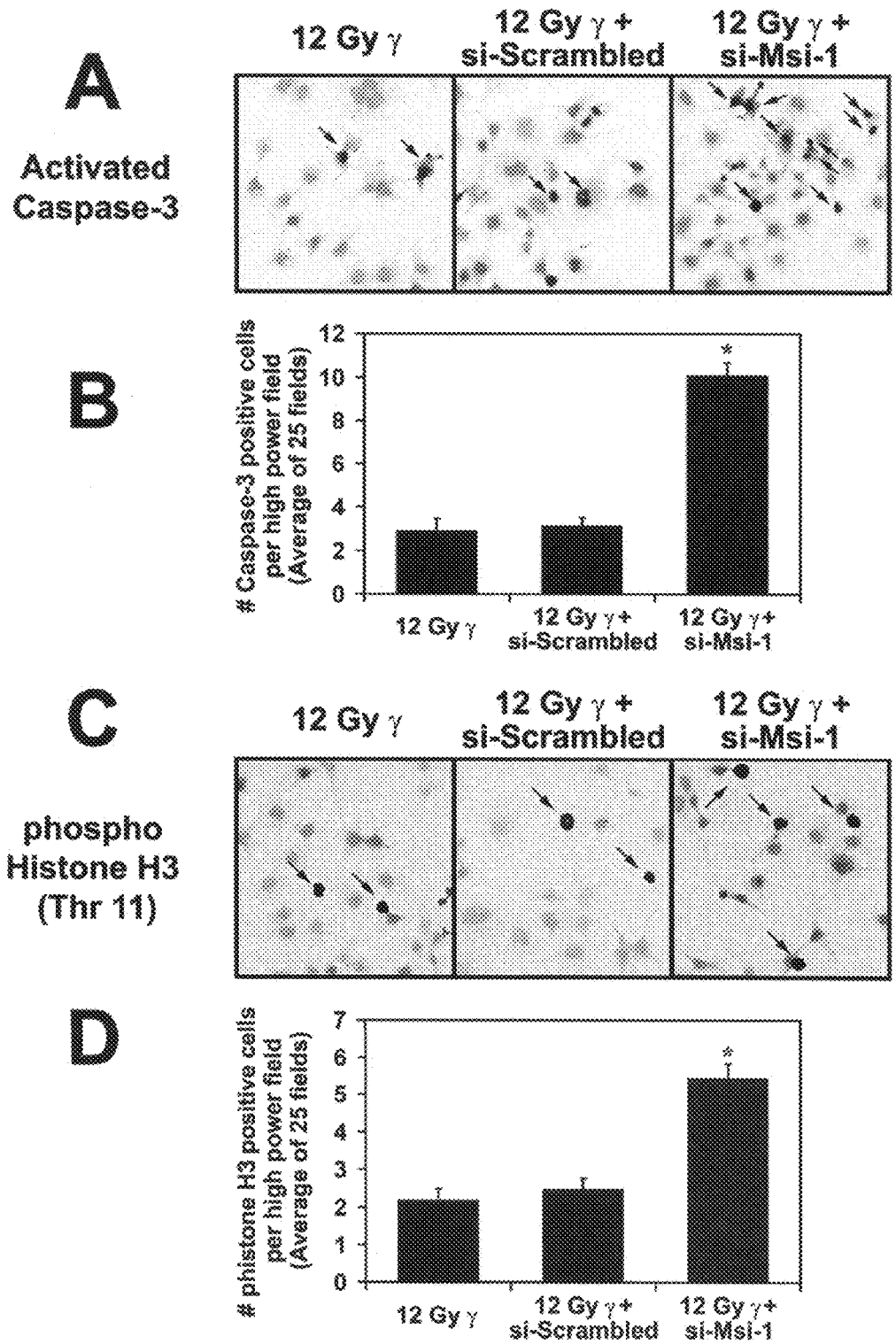

FIG. 5 demonstrates that knockdown of Msi-1 augments radiation induced apoptosis. HCT116 cells transfected with 30 nM si-Msi-1 #1 or si-scrambled for 48 h was subjected to 12 Gy γ-radiation. Then the cells were fixed and stained for activated caspase-3 (A) The cells positive for activated caspase-3 indicated by the arrows were quantified and represented as an average of 25 high power fields (B) Error bars indicate the SEM; * p<0.01. (C) The siRNA transfected cells followed by radiation were subjected to staining for phosphorylated histone H3. The cells positive for phosphorylated histone H3 are indicated by the arrows. (D) The cells quantified are represented as an average of 25 high power fields. Error bars indicate the SEM; * p<0.01.

Figure 6:
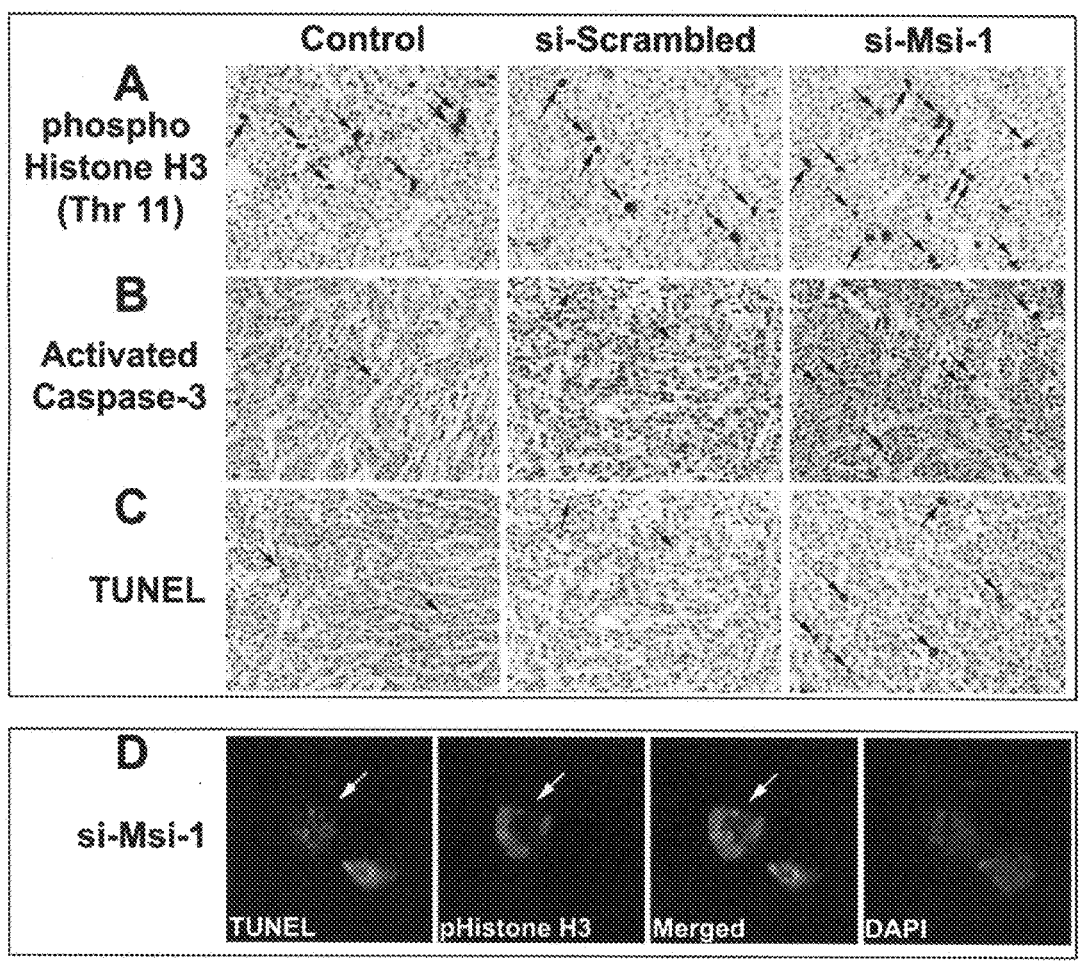

FIG. 6 demonstrates that knockdown of Msi-1 leads to mitotic catastrophe in the tumors. The control, si-scrambled or si-Msi-1 treated tumors were subjected to immunohistochemical staining for phosphorylated histone H3 (A), activated caspase-3 (B), TUNEL (C). The cells positive for the above are indicated by the arrows in the particular photograph. (D) si-Msi-1 treated tumors were subjected to immunofluorescence staining for TUNEL (Green) and phosphorylated histone H3 (Red). The cell positive for TUNEL and phosphorylated histone H3 in the merged image is indicated by the arrow. The nucleus was stained with DAPI.

FIG. 7 demonstrates that downregulation of Msi-1 leads to increased mitosis and apoptosis. (A) Msi-1 siRNA treated tumor xenografts co-stained for Msi-1 and phosphorylated histone H3 demonstrate that cells positive for phosphorylated histone H3 (Green) is negative for Msi-1 (Red). Nucleus was stained with Hoechst 33342 (Blue). (B) The cells positive for TUNEL (Green) are negative for Msi-1 (Red) in the tumor xenografts stained with Hoechst 33342 (Blue).

FIG. 8 demonstrates that siRNA mediated knockdown of Msi-1 leads to a decrease in Notch-1 and increase in $p21^{WAF1}$. The control (A), scrambled siRNA treated (B) and Msi-1 siRNA treated (C) tumors were stained for Notch-1. The brown staining demonstrate cells positive for Notch-1. The arrow in the control or tumors treated with scrambled siRNA indicates a representative cell positive for cytoplasmic and nuclear Notch-1. The tumors treated with Msi-1 siRNA demonstrated a loss of Notch-1 staining. (D) HCT116 cells were transfected with (10 and 50 nM) of Msi-1 siRNA or with 50 nM of scrambled siRNA for 72 h. The cells were lysed and subjected to western blot analyses for Notch-1. The representative blot shown demonstrates decreased Notch-1 and cleaved Notch-1 expression in the cells treated with si-Msi-1 compared to control or si-scrambled treated HCT116 cells. Actin was used as loading control. Control transfection reagent (E), scrambled siRNA treated (F) and Msi-1 siRNA treated (G) tumors were stained for $p21^{WAF1}$. The brown staining demonstrate cells positive for $p21^{WAF1}$. The arrow in the control tumors or tumors treated with scrambled siRNA indicates a representative cell positive for $p21^{WAF-1}$. The tumors treated with Msi-1 siRNA demonstrated increased expression of $p21^{WAF-1}$ immunostaining. (H) Control, scrambled siRNA and Msi-1 siRNA treated tumor xenografts were lysed and subjected to western blot analyses for $p21^{WAF-1}$. The representative blot shown demonstrates increased $p21^{WAF-1}$ expression in the cells treated with si-Msi-1 compared to control or si-scrambled treated tumor xenografts. Actin was used as loading control.

Figure 9:
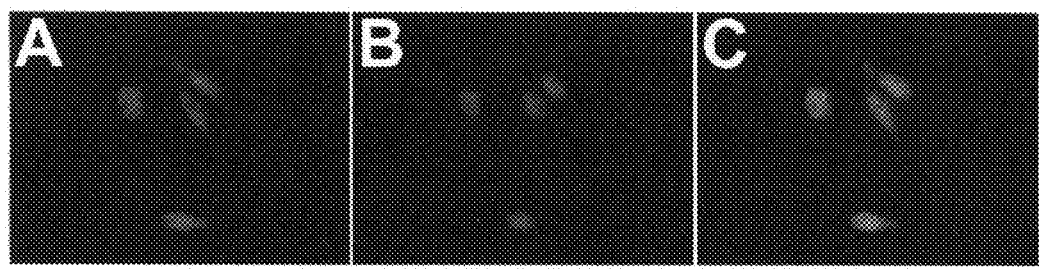

FIG. 9 demonstrates expression of CD133/AC133 in HCT116 cells. HCT116 cells were immunostained for CD133/AC133 antibody. The cells positive for CD133/AC133 are stained red (A). The nucleus was stained using Hoechst 33342 (blue) (B). (C) Merged image of (A) and (B).

Figure 10:
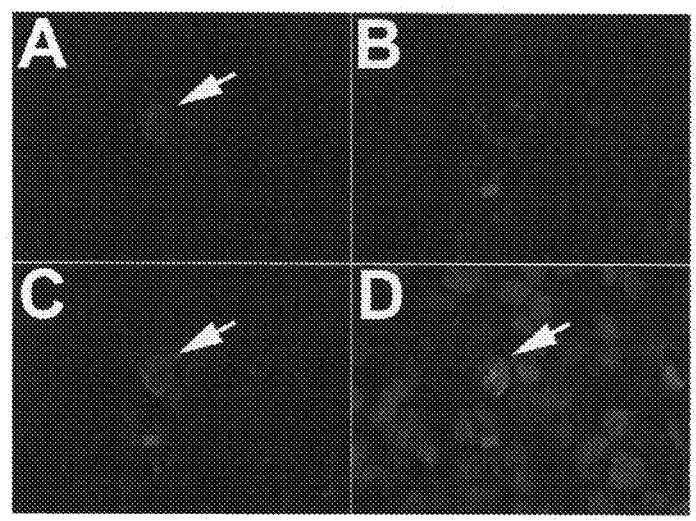

FIG. 10 demonstrates expression of CD133/AC133 in tumor xenograft. The control tumor xenograft was immunohistologically stained for Msi-1 (green) indicated by the arrow (A), CD133/AC133 (red) (B). (C) Cell positive for both Msi-1 and CD133/AC133 is indicated by the arrow in the merged image of (A) and (B). (D) Merged image of (A) (B) and (C), the cell positive for Msi-1, CD133/AC133 is indicated by the arrow.

Figure 11:
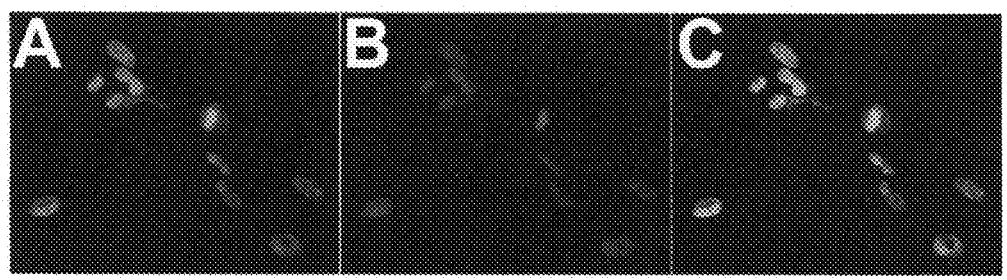

FIG. 11 demonstrates expression of Msi-2 in HCT116 cells. HCT116 cells were immunostained for Msi-2 antibody. The cells positive for Msi-2 are stained green (A). The nucleus was stained using Hoechst 33342 (blue) (B). (C) Merged image of (A) and (B).

Figure 12:
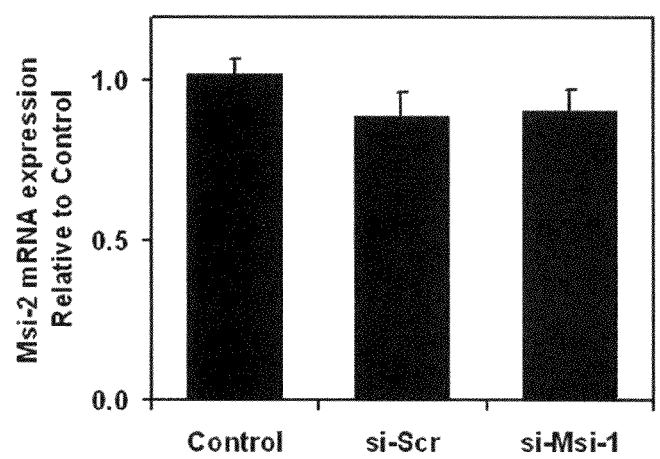

FIG. 12 demonstrates expression of Msi-2 in tumor xenograft. Total RNA isolated from control, scrambled siRNA and Msi-1 siRNA treated tumor xenografts was subjected to real-time RT PCR for Msi-2. n=5; error bars represent 95% confidence interval.

Figure 13:
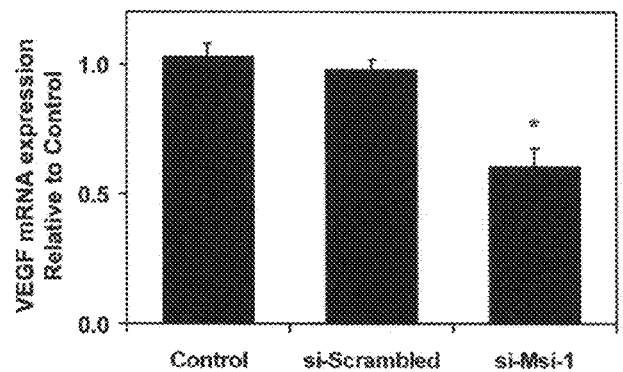

FIG. 13 demonstrates that siRNA mediated knockdown of Msi-1 results in downregulation of VEGF in HCT116 tumor xenografts compared to Control or si-scrambled treated tumors. *p=0.05.

Figure 14:
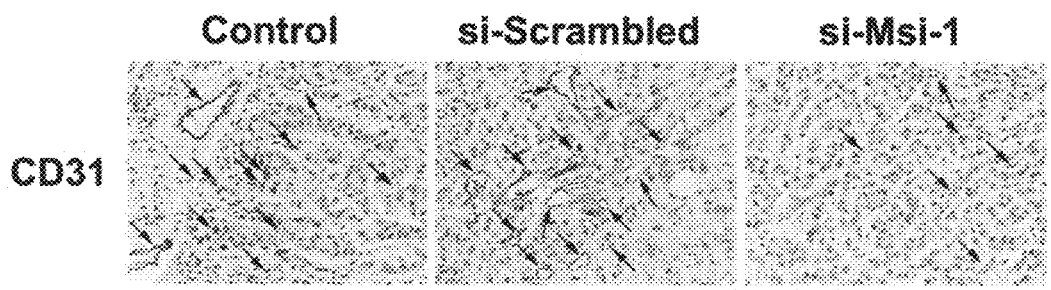

FIG. 14 demonstrates that lack of msi-1 leads to reduction of angiogenesis in the tumors. The control untreated, si-scrambled or si-Msi-1 treated tumors were subjected to immunohistochemical staining for CD31. The cells positive for CD31 are indicated by the arrows.

Figure 15:
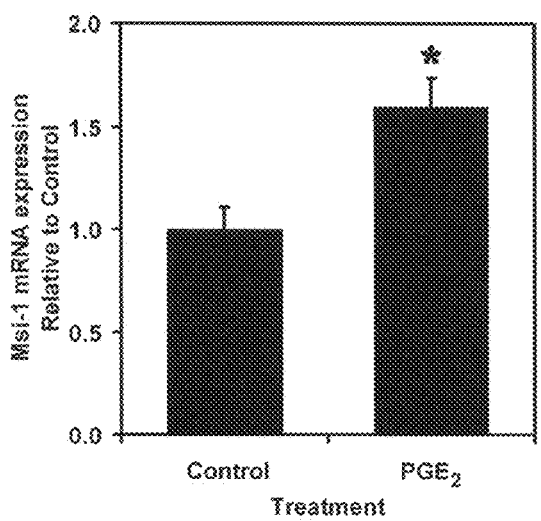

FIG. 15 demonstrates that $PGE_2$ induces Msi-1. HCT116 cells were treated with $PGE_2$, and total RNA isolated was subject to real-time RT PCR for Msi-1 mRNA expression. Following treatment with $PGE_2$, 1.6 fold increase in Msi-1 mRNA was observed. *p=0.05.

DETAILED DESCRIPTION OF THE INVENTION

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell. These short dsRNA molecules, called "short interfering RNA" or "siRNA," cause the destruction of messenger RNAs ("mRNAs") which share sequence homology with the siRNA. It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Specific methods of using siRNAs are described in detail in U.S. Pat. Nos. 7,345,027, issued to Tolentino et al. on Mar. 18, 2008; 7,148,342, issued to Tolentino et al. on Dec. 12, 2006; 7,511,025, issued to Wyatt et al. on Mar. 31, 2009; and 7,511, 132, issued to Khvorova et al. on Mar. 31, 2009; the entire contents of such patents are expressly incorporated herein by reference. These patents describe siRNAs which specifically target and cause RNAi-induced degradation of mRNA, such as RNA from VEGF and VEGF receptors, MMP-1 and BCL-2, respectively, and such siRNA compounds may be used to suppress invasion and/or metastasis of tumor cells and/or inhibit angiogenesis, in particular for the treatment of cancerous tumors, age-related macular degeneration, and other angiogenic diseases. The methods of these patents may be applied to the production and use of siRNAs in accordance with the presently disclosed and claimed invention.

As used herein, the term "anticancer agent" refers to a molecule capable of inhibiting cancer cell function. The agent may inhibit proliferation or may be cytotoxic to cells. A variety of anticancer agents can be used and include those that inhibit protein synthesis and those that inhibit expression of certain genes essential for cellular growth or survival. Anticancer agents include those that result in cell death and those that inhibit cell growth, proliferation and/or differentiation. In one embodiment, the anticancer agent may be selectively toxic against certain types of cancer cells but does not affect or is less effective against other normal cells. In another embodiment, the anticancer agent is an antineoplastic agent.

The term "antineoplastic agent" is used herein to refer to agents that have the functional property of inhibiting a development or progression of a neoplasm in a human or animal, particularly a malignant (cancerous) lesion, such as a carcinoma, sarcoma, lymphoma, or leukemia. Inhibition of metastasis is frequently a property of antineoplastic agents.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the invention. The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the pharmaceutical compositions of the presently disclosed and claimed invention. This concurrent therapy can be sequential therapy where the patient is treated first with one drug and then the other, or the two drugs are given simultaneously.

The terms "administration" and "administering", as used herein will be understood to include all routes of administration known in the art, including but not limited to, oral, topical, transdermal, parenteral, subcutaneous, intranasal, mucosal, intramuscular and intravenous routes, including both local and systemic applications. In addition, the methods of administration may be designed to provide delayed or controlled release using formulation techniques which are well known in the art.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

A "liposome" is a small vesicle composed of various types of lipids, phospholipids and/or surfactant. The components of the liposome are commonly arranged in a bilayer formation, similar to the lipid arrangement of biological membranes.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "patient" as used herein includes human and veterinary subjects. "Mammal" for purposes of treatment refers to any animal classified as a mammal, including human, domestic and farm animals, nonhuman primates, and any other animal that has mammary tissue.

The terms "treat", "treating" and "treatment", as used herein, will be understood to include both inhibition of tumor growth as well as induction of tumor cell death.

As used herein, the term treating cancer or treatment of cancer means to inhibit the spread of cancer, decrease tumor size, lessen or reduce the number of cancerous cells in the body, or ameliorate or alleviate the symptoms associated with the cancer. The treatment is considered therapeutic if there is a decrease in mortality and/or morbidity, or a decrease in disease burden manifested by reduced numbers of malignant cells in the body.

Preventing cancer or prevention of cancer is intended to mean preventing the occurrence or recurrence of the disease state of cancer. As such, a treatment that impedes, inhibits, or interferes with metastasis, tumor growth, or cancer proliferation is deemed preventive.

As used herein, managing cancer encompasses preventing the recurrence of cancer in a patient who had suffered from cancer, lengthening the time a patient remains in remission, preventing the occurrence of cancer in patients at risk of suffering from cancer (e.g., patients who had been exposed to high amounts of radiation or carcinogenic materials; patients infected with viruses associated with the occurrence of cancer; and patients with genetic predispositions to cancer), and preventing the occurrence of malignant cancer in patients suffering from pre-malignant or non-malignant cancers.

Administering a therapeutically effective amount or prophylactically effective amount is intended to provide a therapeutic benefit in the treatment, prevention, or management of cancer. The specific amount that is therapeutically effective can be readily determined by the ordinary medical practitioner, and can vary depending on factors known in the art, such as the type of cancer, the patient's history and age, the stage of cancer, the co-administration of other anti-cancer agents, including radiation therapy.

The presently disclosed and claimed invention is related to methods of inhibiting tumor growth. Such methods involve an inhibition of one or more RNA binding proteins in the tumor cells. In one embodiment, the RNA binding protein is Musashi-1 (Msi-1). Such methods of inhibition of RNA binding proteins results in a decrease in cancer cell proliferation and apoptosis, as well as $G_2$/M arrest, coupled with mitotic catastrophe. Inhibition of RNA binding proteins may also result in a decrease in mRNA stability and/or translation for at least one of the vascular endothelial growth factor (VEGF), interleukin-8 (IL-8), cyclooxygenase-2 (COX-2), Notch-1 and matrix metalloproteinase 7 (MMP7) gene products.

The expression of said RNA binding proteins can be inhibited using any well known method that targets the RNA binding protein's gene or its mRNA. These methods include, but are not limited to, the use of antisense oligonucleotides, ribozymes, nucleic acid molecules that promote triple helix formation, and short-interfering RNAs (siRNAs) or co-repression of a target gene by introducing a homologous gene fragment into the cell that harbors the target gene. In particular embodiments, the methods of the presently disclosed and claimed invention employ siRNAs that specifically reduces expression of the RNA binding protein.

In one embodiment, the expression of at least one RNA binding protein is inhibited by the use of an RNA interference technique referred to as RNAi. RNAi allows for the selective knockout of a target gene in a highly effective and specific manner. This technique involves introducing into a cell double-stranded RNA (dsRNA), having a sequence corresponding to the exon portion of the target gene. The dsRNA causes a rapid destruction of the target gene's mRNA.

RNAi can be performed, for example, using chemically-synthesized RNA. Alternatively, suitable expression vectors can be used to transcribe such RNA either in vitro or in vivo. In vitro transcription of sense and antisense strands (encoded by sequences present on the same vector or on separate vectors) can be effected using for example T7 RNA polymerase, in which case the vector can contain a suitable coding sequence operably-linked to a T7 promoter. The in vitro-transcribed RNA can, in certain embodiments, be processed (e.g., using E. coli RNase III) in vitro to a size conducive to RNAi. The sense and antisense transcripts are combined to form an RNA duplex which is introduced into a target cell of interest. Other vectors can be used, which express small hairpin RNAs (shRNAs) which can be processed into siRNA-like molecules. Various vector-based methods are described in, for example, Brummelkamp, et al. (2002) Science 296(5567): 550-3; Lee, et al. (2002) Nat. Biotechnol. 20(5):500-5; Miyagashi and Taira (2002) Nat. Biotechnol. 20(5):497-500; Paddison, et al. (2002) Proc. Natl. Acad. Sci. USA 99(3):1443-8; Paul, et al. (2002); and Sui, et al. (2002) Proc. Natl. Acad. Sci. USA 99 (8):5515-20. Various methods for introducing such vectors into cells, either in vitro or in vivo (e.g., gene therapy), are known in the art.

Kits for production of dsRNA for use in RNAi are available commercially, e.g., from New England Biolabs, Inc. and Ambion Inc. (Austin, Tex., USA). Methods of transfection of dsRNA or plasmids engineered to make dsRNA are routine in the art.

The methods described herein may be utilized for treatment of any cancer, including but not limited to, cancers of the colon, pancreas, breast, prostate, lung and ovaries. Particular cancers that can be treated and managed by the methods of the presently disclosed and claimed invention include, but are not limited to, those associated with an increase in the expression of at least one RNA binding protein, including but not limited to, Musashi-1 (Msi-1).

The presently disclosed and claimed invention is directed to a short-interfering ribonucleic acid (siRNA) molecule effective at silencing Musashi-1 (Msi-1) expression. The siRNA molecule comprises a sense RNA strand and an antisense RNA strand, wherein the sense and antisense RNA strands form an RNA duplex, and wherein the sense RNA strand comprises a nucleotide sequence identical to a target sequence of about 15 to about 25 contiguous nucleotides in Msi-1 mRNA (or a homolog thereof). The Msi-1 target sequence that binds the siRNA can be selected experimentally or empirically. In certain embodiments, the Msi-1 mRNA may be in accordance with SEQ ID NO:1, and the sense RNA strand may comprise at least one of SEQ ID NOS:2 and 3.

Alternatively, depending on the conditions under which binding is sufficient to disrupt the function of the Msi-1 gene, a sequence complementary to a target sequence within the Msi-1 nucleic acid sequences need not be 100 percent identical to the target sequence. For example, a sequence can be complementary to its target sequence when at least about 80 or 90 percent of its nucleotides bind via matched base pairings with nucleotides of the target sequence.

Therefore, the sense RNA strand may comprise a sequence homologous to a portion of SEQ ID NO:1 that is capable of hybridizing to its target sequence under stringent conditions. In general, for complementary sequences to hybridize under stringent conditions, said sequences are at least 80 or 90 percent identical to each other. One non-limiting example of stringent hybridization conditions includes 6× sodium chloride/sodium citrate (SSC) at about 45° C., followed by 0.2× SSC, 0.1% SDS at 50-65° C. Thus, the presently disclosed and claimed invention also includes siRNAs having a sense RNA strand that comprises a nucleotide sequence that is at least 90% identical to a target sequence of about 15 to about 25 contiguous nucleotides in Msi-1 mRNA (or a homolog thereof).

The siRNAs of the presently disclosed and claimed invention may include modifications to their sugar-phosphate backbone or nucleosides. These modifications can be tailored to promote selective genetic inhibition, while avoiding a general panic response reported to be generated by siRNA in some cells. Moreover, modifications can be introduced in the bases to protect siRNAs from the actin of one or more endogenous degradative enzymes.

The presently disclosed and claimed invention also includes a pharmaceutical composition comprising said siRNA molecule. The pharmaceutical composition may further comprise at least one additional chemotherapeutic agent, as described in detail herein. In addition, the pharmaceutical composition may also further comprise a delivery agent, such as but not limited to, a liposome.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the agents of the invention from degradation within the gastrointestinal tract. In another example, the agents of the invention may be administered in a liposomal formulation to shield the agents from degradative enzymes, facilitate transport in circulatory system, and effect delivery across cell membranes to intracellular sites.

The composition, shape, and type of dosage forms of the pharmaceutical compositions of the presently disclosed and claimed invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by the invention will vary from one another and will be readily apparent to those skilled in the art. See, e.g., Remington: The Science and Practice of Pharmacy, Alfonso R. Gennaro, editor, 20th ed. Lippincott Williams & Wilkins: Philadelphia, Pa., 2000.

The presently disclosed and claimed invention also includes a method of inhibiting expression of Musashi-1 (Msi-1) protein. Said method includes providing a cell expressing Msi-1 and providing the siRNA molecule described herein above; the cell is then contacting with the siRNA, thereby specifically inhibiting the expression of Msi-1.

The presently disclosed and claimed invention also includes a method of inhibiting expression of Musashi-1 (Msi-1) protein in a subject. In said method an effective amount of the pharmaceutical composition described herein above is administered to the subject, thereby specifically inhibiting the expression of Msi-1.

The presently disclosed and claimed invention further includes a method of inhibiting tumor growth. In said method, the siRNA described herein above is provided and contacted with the tumor, thereby specifically inhibiting the expression of Msi-1 in the tumor and thus inhibiting growth of the tumor. Said method may result in at least one of a decrease in cancer cell proliferation, apoptosis, $G_2/M$ arrest, mitotic catastrophe and a decrease in at least one of mRNA stability and mRNA translation for Notch-1.

The presently disclosed and claimed invention also includes a method of inhibiting tumor growth in a subject, which includes providing the pharmaceutical composition described herein above and administering an effective amount thereof to the subject, thereby specifically inhibiting the expression of Msi-1 in the tumor and thus inhibiting growth of the tumor. Said method may result in at least one of a decrease in cancer cell proliferation, apoptosis, $G_2/M$ arrest, mitotic catastrophe and a decrease in at least one of mRNA stability and mRNA translation for Notch-1.

Delivery of the agents of the presently disclosed and claimed invention (e.g., siRNAs) into a patient can either be direct, i.e., the patient is directly exposed to an agent of the invention or agent-carrying vector, or indirect, i.e., cells are first transformed with the nucleic acid sequences encoding an agent of the invention in vitro, then transplanted into the patient for cell replacement therapy. These two approaches are known as in vivo and ex vivo therapy, respectively.

The presently disclosed and claimed invention is also directed to a method of generating a tumor cell. Such method includes providing at least one of a primary cell and an immortalized cell, and introducing a gene encoding an RNA binding protein into the cell such that the cell overexpresses the RNA binding protein and exhibits increased cell proliferation and induction of anchorage independent growth. Such generated tumor cell may then be utilized as a model system for identifying novel therapeutics for cancer therapy.

The presently disclosed and claimed invention is also directed to a diagnostic method for cancer detection, progression and/or prognosis. Such diagnostic method involves the detection of an RNA binding protein, such as but not limited to, Musashi-1, as a marker. The method may also include detection of the specific level of RNA binding protein present and comparison thereof to known levels of RNA binding protein present in normal cells and in cells at various stages of tumor progression and/or metastasis.

Examples are provided hereinbelow. However, the presently disclosed and claimed invention is to be understood to not be limited in its application to the specific experimentation, results and laboratory procedures. Rather, the Examples are simply provided as one of various embodiments and are meant to be exemplary, not exhaustive.

Example 1

The present Example demonstrates that Msi-1 expression is upregulated in human colorectal tumors compared with its paired uninvolved tissue. siRNA-mediated knockdown of Msi-1 in the tumor xenografts resulted in the arrest of tumor growth. Furthermore, inhibition of Msi-1 resulted in decreased cancer cell proliferation, increased caspase-3-mediated apoptosis alone, and enhanced radiation-induced apoptosis. However, there was increased staining for phosphorylated histone H3 (a marker of mitosis) and colocalization of terminal deoxynucleotidyl transferase-mediated deoxyuridine triphosphate nick-end labeling (TUNEL) staining in phosphorylated histone H3 immunoreactive cells, particularly in the tumor xenografts, suggestive of mitotic catastrophe. Furthermore, siRNA mediated down-regulation of Msi-1 resulted in a shift towards the $G_2/M$ phase of the cell cycle. Furthermore, there was down-regulation of Notch-1 and activated Notch-1, and up-regulation of p21$^{WAF1}$ after downregulation of Msi-1. These results support a novel role for Msi-1 in intestinal tumorigenesis as a cell proliferation regulator and inhibitor of mitotic catastrophe.

Materials and Methods for Example 1

Cell culture: HCT116 and HT29 human colon adenocarcinoma cell lines were obtained from the American type culture collection (ATCC) and grown in Dulbecco's modified eagle's medium (DMEM) supplemented with 10% fetal bovine serum and 100-U/mL penicillin-streptomycin in a humidified chamber at 37° C. with 5% $CO_2$.

Silencer RNA: Msi-1 siRNA (si-Msi-1) sequence targeting the coding region of Msi-1 (Accession #_002442; SEQ ID NO:1) was (#1-CUUUUGGAUUUGUGCAU (SEQ ID NO:2) and #2-ACAUCGUGGAGAAAGUG (SEQ ID NO:3)) and scrambled control siRNAs (si-scrambled) not matching any of the human genes was obtained (Ambion Inc., Austin, Tex.) and transfected using Transfectol™ (Ambion Inc.).

Human colorectal carcinoma specimens: Total RNA isolated from human colorectal specimens and its paired uninvolved tissues were provided by Dr. Howard L. McLeod at the University of North Carolina, which was obtained from Tissue Procurement Core of the Siteman Cancer Center, Washington University.

Real Time PCR Analyses: Total RNA isolated either from cells or human colon cancer tumors and its paired uninvolved tissues or from human colon cancer cell tumor xenograft samples were subjected to reverse transcription with Superscript™ II RNase H—Reverse Transcriptase and random hexanucleotide primers (Invitrogen, Carlsbad, Calif.). The cDNA was subsequently used to perform Real Time PCR by SYBR chemistry (SYBR® Green I; Molecular Probes) for specific transcripts using gene specific primers and Jumpstart Taq DNA polymerase (Sigma-Aldrich, St. Louis, Mo.). The crossing threshold value assessed by Real Time PCR was noted for the transcripts and normalized with β-actin mRNA. The changes in mRNA expression were expressed as fold change relative to control with ±SEM value.

Primers used are:

```
β-actin:                                  (SEQ ID NO: 4)
Forward:  5'-GGTGATCCACATCTGCTGGAA-3',
                                          (SEQ ID NO: 5)
Reverse:  5'-ATCATTGCTCCTCCTCAGGG-3', Msi-1:                                    (SEQ ID NO: 6)
Forward:  5'-CAGTTTCGGACCTATCTCTGAGGT-3',
                                          (SEQ ID NO: 7)
Reverse:  5'-AAGGTGATGAAACCAAAACCCCT-3', Msi-2:                                    (SEQ ID NO: 8)
Forward:  5'-TGAGCTGGCAGACCTCACCA-3',
                                          (SEQ ID NO: 9)
Reverse:  5'-AAACCGAAGCCTCTGGAGCG-3'.
```

Western Blot analysis: HCT116 cells were cultured in a 6 well plates to 40% confluency and were transfected with si-Msi-1 or si-scrambled for 72 h. Cells or the tumor xenograft samples were lysed and concentration of protein was determined by BCA protein assay kit (Pierce Biotechnology Inc., Rockford, Ill.). Forty μg of the protein was size separated in a 15% SDS polyacrylamide gel and transferred onto a nitrocellulose membrane with a semidry transfer apparatus (Amersham-Pharmacia, Piscataway, N.J.). The membrane was blocked in 5% non-fat dry milk for 1 h and probed overnight with a rabbit anti-Msi-1 antipeptide antibody (Abcam Inc., Cambridge, Mass.) or with goat anti-Notch-1 antibody (Santa Cruz Biotechnology Inc., Santa Cruz, Calif.) or with rabbit anti-p21 antibody (Santa Cruz Biotechnology Inc.). Subsequently the membrane was incubated with anti-rabbit IgG or with anti-goat IgG horseradish peroxidase-conjugated (Amersham-Pharmacia) for 1 h at room temperature. The 39 kDa Msi-1 protein, 21 kDa p21$^{WAF1}$, 300 kDa Notch-1 and 120 kDa cleaved Notch-1 were detected using ECL™ Western Blotting detection reagents (Amersham-Pharmacia). Actin (43 kDa), used as loading control was identified using a goat polyclonal IgG (Santa Cruz Biotechnology Inc., Santa Cruz, Calif.).

Immunohistochemistry: (a) Brightfield: Heat Induced Epitope Retrieval (HIER) was performed on 4 μm paraffin-embedded tumor xenograft sections utilizing a pressurized de-cloaking chamber (Biocare Medical, LLC, Concord, Calif.) and incubated in citrate buffer (pH 6.0) at 99° C. for 18 min. The sections were then washed three times with PBS (Sigma), and endogenous biotin activity was blocked using Avidin/Biotin blocking kit (Vector Lab, Burlingame, Calif.) according to manufacturer's instructions. Further, endogenous peroxidase activity was quenched with 3% hydrogen peroxide. After washing, the slides were then incubated in horse normal serum (2%) and BSA (1%) at room temperature for 20 min to block non-specific binding. The sections were then exposed to primary antibodies [(rabbit anti-Msi-1 (Abcam), rabbit anti-caspase-3 (Cell Signaling, Danvers, Mass.), rabbit anti-phosphorylated histone H3 (Thr-11) (Upstate, Lake Placid, N.Y.), goat anti-Notch-1 (Santa Cruz Biotechnologies) or rabbit antip21$^{WAF1}$ (Santa Cruz Biotechnologies)] overnight at 4° C. Slides were then washed three times with PBS and incubated in the appropriate secondary antibody biotinylated donkey anti-rabbit, donkey anti-goat (Jackson Immuno Research Lab, West Grove, Pa.) for 30 min at room temperature. Slides were washed again and then incubated in Streptavidin-HRP (Dako, Carpinteria, Calif.) at room temperature for 12 min. After final wash in PBS, chromogenic development was performed utilizing DAB substrate (Sigma). TUNEL staining was performed using In situ Cell Death Kit (Roche diagnostics, Indianapolis, Ind.) according to the manufacturer's instructions, and the POD converter was utilized to enable DAB chromogenic development. All slides were counterstained with hematoxylin (Biocare Medical), dehydrated in graded alcohols, cleared in xylene, and permanently mounted with cryoseal (Richard-Allen, Kalamazoo, Mich.). (b) Fluorescence: HIER was performed on 4 μm paraffin-embedded tumor xenograft sections utilizing a pressurized de-cloaking chamber (Biocare Medical, LLC) and incubated in citrate buffer (pH 6.0) at 99° C. for 18 min. After washing three times with PBS, the slides were then incubated in horse normal serum (2%) and BSA (1%) at room temperature for 20 min to block non-specific binding. Sections were then sequentially exposed to rabbit phosphorylated histone H3 (Upstate) or rabbit Musashi-1 (Abcam) for 1 h at 30° C. and its appropriate secondary fluorescent conjugate alexa fluor 488 (green) or alexa fluor 568 (red) (Invitrogen) for 30 min at room temperature wherever indicated. Finally fluorescein conjugated Terminal deoxynucleotidyl Transferase Biotin-dUTP Nick End Labeling (TUNEL) staining was performed using "In situ Cell Death Kit" (Roche diagnostics), according to manufacturer's instructions. The slides were then wet-mounted and counterstained utilizing Vectashield with DAPI (Vector Lab) or with Hoechst 33342 (Invitrogen). (c) Microscopic Examination: Slides were examined using Nikon 80i microscope base. For brightfield, 60× digital images were taken with PlanAPO objective and DXM1200C camera (Nikon, Melville, N.Y.). Fluorescent images were taken with 60× PlanFluoro objective and 2× optical converter for a final magnification of 120×, utilizing CoolSnap ES2 camera (Photometrics, Tucson, Ariz.). Filter sets with excitation ranges for Cy3, FITC, and DAPI were used. All images were captured utilizing NIS-Elements software (Nikon) and further processed using Adobe Photoshop 8.0 software (Adobe Systems Inc., San Jose, Calif.).

Cell Proliferation Assays.

Hexosaminidase assay: Msi-1-targeted siRNA was transfected with 1×10$^4$ HCT116 or HT29 cells and plated simultaneously in a 96 well plates. Cell numbers were estimated at time point 24, 48 and 72 h after 48 h of siRNA transfection using a chromogenic substrate (p-nitrophenyl-N-acetyl-β-D-Glucosaminide) (Sigma-Aldrich). The lysozyme enzyme (N-acetyl-β-D-hexosaminidase) released from the proliferating cells convert the substrate to p-nitrophenyl, which was measured in a microtitre plate reader (Synergy HT, BIOTEK, Winooski, Vt.) at 405 nm (Landegren et al., 1984). The cell numbers were plotted as mean±SEM of 3 different experiments. The Students t test was used to calculate the statistical significance.

MTT assay: Msi-1-targeted siRNA was transfected with 1×10$^4$ HCT116 cells and plated simultaneously in 96 well plates. Cell numbers were estimated at time point 72 h after 48 h of siRNA transfection using 50 μg of 3-[4,5-dimethylthiazol-2-yl]-2,5-diphenol tetrazolium bromide (MTT) assay. 10 μl of MTT (5 mg/ml) (Invitrogen) was added to each well, and the plates were incubated at 37° C. for 2 h. Then, 100 μL of solubilization solution (20% SDS, 50% dimethyl formamide, 2% acetic acid and 0.1N HCl in anhydrous isopropanol) was added, and the solution was pipetted up and down to dissolve the crystals. Absorbance was measured spectrophotometrically at a dual wavelength of 570 and 405 nm (Mosmann et al., 1983; and Agarwal et al., 1999).

Flow Cytometric analysis. HCT116 cells were transfected with 30 nM si-Msi-1 or si-scrambled for 72 h. The control and transfected cells were washed twice with ice-cold phosphate buffered saline (PBS) and harvested by trypsinization and further washed 6 times with PBS. The single-cell suspensions were fixed using 70% ethanol for 2 h. The cells were centrifuged to remove the 70% ethanol and washed with PBS. The ethanol fixed cells was permeabilized with PBS containing 1 mg/ml propidium iodide (Sigma-Aldrich), 0.1% triton X-100 (Sigma-Aldrich) and 2 mg DNase-free RNase (Sigma-Aldrich) at room temperature. Flow cytometry was done with a FACSCalibur analyzer 3-color (Becton Dickinson, Mountain, View, Calif.), capturing 50,000 events for each sample; results were analyzed with ModFit LT™ software (Verity Software House, Topsham, Me.).

Xenograft tumor model. (a) Liposomal preparation: siRNA was administered into the xenografts after incorporation into 1,2-Dioleoyl-sn-Glycero-3-Phosphocholine (DOPC) (Avanti Polar Lipids, Alabaster, Ala.). DOPC and siRNA were mixed in the presence of excess tertiary butanol at a ratio of 1:10 (w/w) (siRNA/DOPC). TWEEN® 20 (Sigma-Aldrich) was added to the mixture in a ratio of 1:19 TWEEN® 20: siRNA/DOPC. The mixture was vortexed and frozen in an acetone/dry ice bath and lyophilized. Before administration, the siRNA preparation was reconstituted in 0.9% sterile saline and injected at a dose of 50 μl (5 μM) per injection. (b) Tumor therapy: Female athymic nude mice (NCr-nu) were purchased from the National Cancer Institute-Frederick Cancer Research and Development Center (Frederick, Md.) and housed in specific pathogen-free conditions. They were cared for in accordance with guidelines set forth by the American Association for Accreditation of Laboratory Animal Care and the USPHS "Policy on Human Care and Use of Laboratory Animals," and all studies were approved and supervised by the Institutional Animal Care and Use Committee. HCT116 cells (6×10$^6$) cells were injected subcutaneously into the flanks of 4-6 week-old female athymic nude mice (5 mice per group). Tumors were measured with calipers and calculated volume as (length×width$^2$)×0.5. The tumors reached 500 mm$^3$ after 15 days of injection of cells. These tumors were injected with 50 μl (5 μM) of siRNA preparation on every third day from day 15 for a total of 5 doses.

Results for Example 1

Msi-1 is expressed in human colorectal tumor and knockdown inhibits growth of tumor xenografts. Msi-1 is overexpressed in APC$^{min/+}$ mice tumors compared to uninvolved tissue (Potten et al., 2003). To determine the expression of Msi-1 in human colorectal tumors, total RNA was isolated from resection specimens of patients with colonic or rectal adenocarcinoma. The RNA from the tumors and the paired surrounding uninvolved tissue were subjected to real-time RT PCR for Msi-1. A greater than 2 fold increase (p<0.01) of Msi-1 mRNA expression was found in 10 out of 15 tumor specimens, compared to its paired uninvolved tissues (FIG. 1A). In order to determine the role of Msi-1 in tumor progression, tumor xenografts were generated by injecting HCT116 cells subcutaneously into athymic nude mice and injected those tumors with siRNA targeted against human Msi-1 (si-Msi-1), scrambled siRNA (si-scrambled) or transfection reagent/carrier alone (Control). The tumor volume was calculated at various time points. Administration of si-Msi-1 arrested HCT116 colon adenocarcinoma tumor xenograft growth. Moreover, si-Msi-1 treated tumors (average tumor volume of 899.2±517.4 mm$^3$) were considerably smaller than the control (4124.3±1301.1 mm$^3$) or the si-scrambled treated tumors (6225.7±638.18 mm$^3$). The inhibition produced by si-Msi-1 was statistically significant (p<0.05) compared to control or (p<0.01) compared to si-scrambled treated tumors (FIG. 1B). Total RNA isolated from these tumors was subjected to real-time RT PCR and demonstrated a significant (60%) downregulation of Msi-1 mRNA expression in the si-Msi-1 treated tumors compared to control or si-scrambled treated tumors (FIG. 1C). Similarly, reduced expression of Msi-1 protein was found in those tumors as demonstrated by the western blot analyses (FIG. 1D) and by immunohistochemistry (FIG. 1E).

Downregulation of Msi-1 results in reduced cancer cell proliferation. Given the reduction in tumor size following knockdown of Msi-1, the possibility that downregulation of Msi-1 affects cancer cell proliferation was tested next. To demonstrate knockdown of Msi-1 in the cells following transfection with 2 different siRNAs, si-Msi-1 (si-Msi-1 #1—used in tumor xenograft study) and si-Msi-1 #2 and si-scrambled, total RNA isolated from these cells was subjected to real-time RT PCR. A significant down regulation of Msi-1 mRNA was noted at 10 and 50 nM of both si-Msi-1 #1 and #2. At 50 nM, there was more than 60% reduction in expression (FIG. 2A). si-Msi-1 #1 and si-Msi-1 #2 demonstrated a dose dependent decrease in Msi-1 protein as demonstrated by Western blot analyses (FIG. 2B). Scrambled siRNA did not inhibit Msi-1 mRNA or protein expression. Subsequently, the impact of siRNA transfection on cell proliferation in HCT116 and HT29 colon cancer cells was investigated. It was noted that proliferation of the HCT116 cells was significantly inhibited when Msi-1-targeted siRNAs was transfected into cells (FIG. 2C). A significant (p<0.01) reduction in HCT116 cell proliferation was observed when two different si-Msi-1 were used at a concentration of 30 nM. The total numbers of cells in the si-Msi-1 transfected cells were 780×10$^3$ cells (si-Msi-1 #1) and 760×10$^3$ cells (si-Msi-1 #2) compared to control (transfection treatment alone) (980×10$^3$) and si-scrambled treated tumors (1068×10$^3$ cells). A subtle increase in proliferation was observed when the cells were transfected with si-scrambled. A significant (p<0.01) reduction (30%) in HT29 colon cancer cell proliferation was also observed following 30 nM siRNA mediated knockdown of Msi-1 (FIG. 2D). One of the tools for validation of siRNA is to adopt 2 or more siRNAs to demonstrate similar activity. Here a total of 3 different si-scrambled (Ambion Inc., and were utilized to transfect HCT116 cells using TRANSFECTOL™ reagent (Ambion Inc.), and proliferation was assessed by hexosaminidase and MTT assays. Similar results were found with both proliferation assays. All the three scrambled siRNAs increased HCT116 cancer cell proliferation by 30%, estimated by both hexosaminidase and MTT assays. There was an increase in proliferation (50%) by the scrambled siRNA in the DOPC transfection reagent used for injecting into tumor xenografts. DOPC transfection reagent alone did not alter the proliferation of HCT116 cells. si-Msi-1 transfected using Transfectol™ or DOPC transfection reagent demonstrated a down regulation of HCT116 cancer cell proliferation (FIG. 3A—Hexosaminidase assay; FIG. 3B—MTT assay).

Knockdown of Msi-1 induces apoptosis, mitosis and G2/M arrest in cancer cells. Additionally, the role of Msi-1 in apoptosis and mitosis was investigated. HCT116 cells transfected with si-Msi-1 and si-scrambled, were fixed and immunostained for activated caspase-3, for measuring apoptosis and phosphorylated histone H3 (Thr-11), a protein that is phosphorylated during mitosis. si-scrambled transfected cells demonstrated minimal activated caspase-3 staining similar to control cells. In contrast, several activated caspase-3 positive cells were noted following si-Msi-1 transfection (FIG. 4A). The number of cells positive for activated caspase-3 was estimated as an average of 25 high power fields. siRNA mediated knockdown of Msi-1 in HCT116 cells demonstrated a 4 fold increase in activated caspase-3 positive cells (FIG. 4B). The HCT116 cells transfected with si-scrambled and si-Msi-1 were also subjected to immunohistochemical staining for phosphorylated histone H3, a marker for mitosis. The si-Msi-1 treated cells demonstrated an increased number (greater than 3 fold) of cells positive for phosphorylated histone H3 compared to control cells or si-scrambled treated cells (FIGS. 4C, D).

To demonstrate the effect of Msi-1 knockdown on cell cycle analysis and control, si-scrambled and si-Msi-1 transfected HCT116 cells were subjected to cell cycle distribution monitored by Fluorescence activated cell sorting (FACS). DNA content was measured by the PI (propidium iodide) staining. There was no change in the $G_2$/M phase of cell cycle distribution in the si-scrambled and control cells, whereas an increased number of cell accumulation in the GSM phase was observed following si-Msi-1 transfection (FIG. 4E). The percentage of cells in each phase was plotted as a bar graph and revealed a significant decrease in the percentage of $G_0$-$G_1$ phase and an increase in $S_1$ phase cells treated with si-scrambled compared to control cells. However, there was a significant decrease in the $G_0$-$G_1$ and $S_1$ phase in si-Msi-1 treated cells. Furthermore, a significant increase in the percentage of cells in GSM was observed following si-Msi-1 transfection (FIG. 4F). Thus, knockdown of Msi-1 resulted in changes in cell cycle distribution compared to control or scrambled si-RNA treated cells.

Knockdown of Msi-1 augments radiation-induced apoptosis. To determine whether si-Msi-1 can sensitize cells to radiation injury, cells transfected with si-scrambled and si-Msi-1 were subjected to 12 Gy γ-irradiation. By 24 h after radiation, cells were evaluated immunohistochemically for activated caspase-3 and phosphorylated histone H3 (Thr 11). si-scrambled treatment did not affect radiation-induced apoptosis, whereas knockdown of Msi-1 increased the number of activated caspase-3 positive cells compared to cells treated with radiation alone (FIG. 5A). There was a 4-fold induction of apoptosis in the si-Msi-1 combined with radiation treated cells compared to cells treated with radiation alone (FIG. 5B). These data demonstrate that si-Msi-1 is an attractive candidate as a potential adjuvant to radiation in the treatment of colon cancer. Similarly, cells were stained for phosphorylated histone H3 to assess mitosis. A nearly 2.3 fold increase in phosphorylated histone H3 staining was observed in cells treated with si-Msi-1 and radiation compared to the cells treated with radiation alone (FIGS. 5C&D). These data further illustrate that knockdown of Msi-1 triggers both apoptosis and mitosis, suggestive of mitotic catastrophe (Castedo et al., 2004; and Ueno et al., 2006).

Knockdown of Msi-1 results in mitotic catastrophe. As a result of the observation that knockdown of Msi-1 resulted in increased apoptosis coupled with mitosis in vitro and given the reduced size of tumors in the xenograft study, the inventors hypothesized that some cells were undergoing mitotic catastrophe. To confirm this, control, si-scrambled and si-Msi-1 treated xenograft tumors were stained for activated caspase-3, TUNEL for detection of apoptosis, and phosphorylated histone H3 for the detection of mitosis. Tumors treated with si-Msi-1 demonstrated an increased number of cells positive for phosphorylated histone H3 (FIG. 6A), activated caspase-3 (FIG. 6B), and TUNEL (FIG. 6C). Furthermore, siRNA mediated knockdown of Msi-1 in the tumors resulted in mitotic catastrophe as evidenced by cells positive for both TUNEL and phosphorylated histone H3 (FIG. 6D). It was found that approximately 20-25% of the apoptotic cells in the tumors undergo mitotic catastrophe following treatment with si-Msi-1.

Furthermore, it was found that most cells positive for phosphorylated histone H3 and TUNEL in the tumor xenografts treated with Msi-1 siRNA were negative for msi-1 as demonstrated by the lack of co-staining (FIG. 7A—Msi-1 co-stained with phosphorylated histone H3; FIG. 7B—Msi-1 co-stained with TUNEL). The nuclear stain was performed using Hoechst 33342.

siRNA mediated downregulation of Msi-1 leads to downregulation of Notch-1 and upregulation of $p21^{WAF1}$. Control, si-scrambled and si-Msi-1 treated tumor xenografts were immunohistochemically stained for Notch-1. Evidence of nuclear and cytoplasmic Notch-1 was found in control and si-scrambled treated tumors, whereas in the tumor xenografts treated with si-Msi-1, there was a loss of Notch-1 staining (FIGS. 8A-C). This was further confirmed by Western blot analyses of cells treated with either si-scrambled or si-Msi-1. Downregulation of Notch-1 and cleaved Notch-1 was also observed by Western blot analysis (FIG. 8D). Next, tumor xenografts were stained for $p21^{WAF1}$. There was increased expression of $p21^{WAF1}$ in tumor xenografts treated with si-Msi-1 compared with control or scrambled siRNA treated tumor xenografts (FIGS. 8E-G). This was further confirmed by Western blot analyses of the tumor xenografts. Upregulation of $p21^{WAF1}$ was found in si-Msi-1 treated tumors compared to control or si-scrambled treated tumors. Actin was used as loading control (FIG. 8H).

Expression pattern of CD133/AC133 in HCT116 cells and tumor xenografts. Human colon cancer-initiating cells (CC-IC) within tumors are capable of initiating and sustaining neoplastic growth. The CD133 positive cell population in colon tumors is thought to identify these cancer initiating cells which exhibit the capacity for self-renewal, differentiation and establishment of tumor heterogeneity (O'Brien et al., 2007; and Ricci-Vitiani et al., 207). HCT116 cells and HCT116 colon cancer tumor xenografts were immunohistochemically stained for CD133. CD133 was found to be ubiquitously expressed in HCT116 cells in tissue culture (FIG. 9). In tumor xenografts, many of the cells were positive for CD133, and a subset of those cells were also positive for Msi-1 (FIG. 10).

Expression of Msi-2 in HCT116 cells and tumor xenografts. Msi-2 is a structural homolog of Msi-1. Msi-2 expression was determined in HCT116 cells. HCT116 cells were immunostained for Msi-2 and found to be ubiquitously expressed (FIG. 11). Msi-2 expression was also determined in xenografts, as was whether Msi-2 expression was affected following knockdown of Msi-1. Total RNA isolated from tumor xenografts was subjected to real-time RT PCR for Msi-2. There was no change in Msi-2 mRNA expression in Msi-1 siRNA treated tumor xenografts compared with control or scrambled siRNA (FIG. 12). This demonstrates that the si-Msi-1 specifically knocks down Msi-1 and not Msi-2. Furthermore, inhibition of tumor growth has no effect on Msi-2.

Discussion of Example 1

There is increasing evidence demonstrating the role of RNA binding proteins in cell proliferation and/or apoptosis by regulating the translation of key factors such as protooncogenes and tumor suppressors. Several RNA binding proteins involved in tumorigenesis are overexpressed during the various stages of cancer. Msi-1, initially identified as a neuronal stem cell marker and more recently identified as a putative intestinal stem cell and early lineage marker, is upregulated in tumors of $APC^{min/+}$ mice (Potten et al., 2003). It has been postulated that gut tumors arise from stem cells expressed at the base of intestinal and colonic crypts. Msi-1, is also upregulated in brain tumors, including medulloblastoma and gliomas (Hemmati et al., 2003; and Yokota et al., 2004). The demonstration of a functional role of Msi-1 in tumorigenesis has implications in stem cell biology as well as cancer research. In the present example, it is demonstrated that expression of Msi-1 mRNA is increased in human colon cancer tumors compared to its paired uninvolved tissue. While each colon tumor differs in its Msi-1 expression, in the present example these data demonstrate that Msi-1 may be involved in majority of the tumor formations. In tumor xenografts derived from HCT116 cells grown in nude mice, treatment with Msi-1 siRNA arrested tumor growth completely and Msi-1 was lost in the treated tumors. These results demonstrate that Msi-1 is an important regulator of tumor growth.

To further understand mechanistically the role of Msi-1 in tumorigenesis, HCT116 cells were transfected with si-Msi-1, and proliferation was assessed. A nearly 30% reduction in proliferation was observed following 45% Msi-1 knockdown. It has been previously demonstrated that Msi-1 enhances cell proliferative capacity through direct binding and regulation of $p21^{WAF1}$ mRNA. Furthermore, overexpression of Msi-1 leads to decreased $p21^{WAF1}$ in HEK293 cells (Battelli et al, 2006). Moreover, following knockdown of Msi-1 in tumor xenografts, upregulation of $p21^{WAF1}$ was observed. Taken together these data demonstrate that Msi-1 regulates cancer cell proliferation. This may be one of the mechanisms responsible for the tumor growth arrest observed in the xenograft model. Thus Msi-1 inhibition has emerged through the presently disclosed and claimed invention as an attractive target for anti-cancer therapy.

In this example, a small increase in cell proliferation was found following si-scrambled transfection. Therefore, 3 si-scrambled siRNAs and 2 Msi-1 siRNAs were tested. The 3 scrambled siRNAs all demonstrated a similar increase in proliferation in cells transfected with TRANSFECTOL™ and DOPC (transfection reagent used for tumor xenograft study) compared to transfection reagent controls. This explains the increased tumor volume following scrambled siRNA treatment of the tumor xenografts compared to treatment with transfection reagent alone. Similarly both Msi-1 siRNAs demonstrated a significant reduction in proliferation compared to scrambled siRNAs and transfection reagent controls. Moreover, the scrambled siRNA demonstrated a decreased $G_0$-$G_1$ population and increased S1 population compared to transfection reagent treatment alone. Taken together, these data demonstrate potential off-target effects of the scrambled siRNA oligo transfection.

Nuclear translocation of Notch may contribute to increased tumorigenesis, by increasing proliferation and inhibiting apoptosis (Artavanis-Tsakonas et al., 1999). Cells over expressing Msi-1 have been reported to demonstrate nuclear translocation of Notch. This is achieved by translational repression of m-Numb, an inhibitor of Notch (Kanemura et al., 2001; Sakakibara et al., 1996; and Imai et al., 2001). In this example, transfecting HCT116 cells with si-Msi-1 lead to increased apoptosis, as evidenced by increased activated caspase-3 and TUNEL staining. Interestingly, there was increased staining for phosphorylated histone H3 (a marker for mitosis) in the cells following knockdown of Msi-1 as well. Furthermore, si-Msi-1 transfection of HCT-116 cells resulted in an increased number of cells at $G_2/M$ phase of the cell cycle. It has been demonstrated that increased expression of $p21^{WAF1}$ leads to apoptosis and $G_2/M$ arrest in various cell lines including human cervical cancer (Niculescu et al., 1998; and Tsao et al., 1999). This example demonstrates that following knockdown of Msi-1, there is increased expression of $p21^{WAF1}$ which leads the cells to $G_2/M$ arrest. In addition, when the cells treated with si-Msi-1 were subjected to radiation injury, an augmentation of apoptosis was observed. Apoptosis caused by reduced Msi-1 leads to $G_2/M$ arrest and mitotic catastrophe by nuclear translocation of cyclin B1 (Curry et al., 2007). Furthermore, although there was evidence of Notch-1 in the nucleus and cytoplasm of the cells in the control or scrambled siRNA treated tumors, this expression was lost in the tumors treated with Msi-1 siRNA. Additionally, there was loss of cleaved Notch-1 in HCT-116 cells transfected with si-Msi-1 even at 10 nM, as demonstrated by Western blot analyses. These data demonstrate that reduction of Msi-1 drives cells to undergo apoptosis/mitotic catastrophe, by reducing Notch-1 expression. This may explain the reduced tumor size in xenografts.

A hallmark of mitotic catastrophe is entry of cells into mitosis despite the presence of damaged DNA, resulting in activation of apoptotic cell death pathway (Ueno et al., 2006). There is evidence that inhibition of Notch signaling leads to mitotic catastrophe. Inhibition of Notch leads to increased G2/M phase arrest, and accumulation of cyclin B1. The initial step in mitotic catastrophe is evidence of apoptosis and DNA damage in a cell, which is undergoing mitosis (Curry et al., 2007). There is evidence that increased expression of Msi-1 increases Notch (Kanemura et al., 2001). It has been shown herein that inhibition of Msi-1 following siRNA transfection in HCT116 cells as well as tumor xenografts lead to inhibition of Notch-1. Furthermore, si-Msi-1 treated tumors demonstrated increased phosphorylated histone H3, activated caspase-3, as well as TUNEL staining. Several cells stained for both phosphorylated histone H3 and TUNEL, with aberrant DAPI staining in the nucleus. There were few caspase-3 positive cells (20-25%) that also stained for phosphorylated histone H3. These cells may represent stem/progenitor-like cells within the tumor and the presence of Msi-1 enhances tumorigenesis, whereas inhibition of Msi-1 in these particular cells leads to mitotic catastrophe (evidenced by absence of Msi-1 in the cells positive for phosphorylated histone H3 and TUNEL), resulting in increased apoptosis and tumor growth arrest.

Recently, colon cancer-initiating cells (CC-IC) have been described (O'Brien et al., 2007; and Ricci-Vitiani et al., 2007), and these cells are a subset of CD133 positive cells within colon cancer tumors. It has been postulated that these cells may define a cancer stem cell population. Msi-1 is a putative stem/progenitor cell marker in the intestine, and both Msi-1 and CD133 expressing cells were demonstrated in tumor xenografts generated from HCT116 cells. Furthermore, there were rare cells where Msi-1 and CD133 were co-expressed. It is tempting to speculate that these cells might represent cancer stem cells or at the very least cancer progenitor cells. Nevertheless, knockdown of Msi-1 results in xenograft tumor growth arrest.

Collectively Example 1 indicates that Msi-1, a putative stem/progenitor cell marker is also an important positive regulator of cell proliferation and inhibitor of apoptosis. Knockdown of Msi-1 in colon cancer cells results in mitotic arrest and simultaneously leads the cell to undergo apoptosis, consistent with mitotic catastrophe. This activity further augments radiation-induced apoptosis. Taken together, these data demonstrates that Msi-1 promotes tumorigenesis by inhibiting mitotic catastrophe particularly in stem/progenitor cells. Furthermore, Msi-1 regulates $p21^{WAF1}$ and Notch-1 signaling, as demonstrated by the siRNA mediated knockdown of Msi-1 that resulted in decreased Notch-1 and cleaved Notch-1 expression with increased expression of $p21^{WAF1}$. These data taken together highlight a previously unappreciated function of Msi-1, and identify Msi-1 as a novel candidate for therapeutic intervention either alone or in combination with radiation therapy.

Example 2 siRNA mediated knockdown of Msi-1 results in reduced angiogenesis. Several reports have demonstrated the positive role of angiogenesis in tumorigenesis (see, for example, Larcher et al., 1998). Several targets that regulate angiogenesis have been identified; vascular endothelial growth factor (VEGF) (Takei et al., 2004) is one among them. Therefore, the effect of Msi-1 on VEGF mRNA expression was analyzed.

Tumor xenografts treated with si-msi-1 demonstrated a significant decrease in VEGF mRNA expression compared with control untreated or si-scrambled treated tumors (FIG. 13). si-msi-1 treated tumors demonstrated a decreased CD31 immunohistochemical staining for micro vessels. Decreases were observed in number as well as size of the blood vessels of si-msi-1 treated tumors compared to the blood vessels associated with control or si-scrambled treated tumors (FIG. 14), as indicated by the arrows. These data demonstrate that msi-1 plays an important role in angiogenesis and that knockdown of msi-1 is beneficial for prevention and/or reduction of angiogenesis.

Prostaglandin $E_2$ ($PGE_2$) induces Msi-1. $PGE_2$, a product of the cyclooxygenase (COX) reaction, stimulates the growth of colonic epithelial cells. Furthermore, $PGE_2$ elevates tumor incidence in various murine models for colorectal cancer (Kawamori et al., 2003; Wang et al., 2004); in addition, cell culture experiments have implicated $PGE_2$ and $PGE_2$ receptor-dependent signaling in the stimulation of colon cancer epithelial cell growth (Shao et al., 2003). In this example, the effect of $PGE_2$ on Msi-1 expression was investigated. HCT116 colorectal cancer cells were treated with 1 μM $PGE_2$ for 1 h. Total RNA isolated was subjected to real-time RT PCR for Msi-1 mRNA expression. A 1.6 fold increase in Msi-1 mRNA was observed following treatment with $PGE_2$ (FIG. 15). This data demonstrates that $PGE_2$ enhances colorectal cancer cell proliferation via enhancement of Msi-1.

Thus, in accordance with the presently disclosed and claimed invention, there has been provided compositions for inhibiting RNA binding proteins, as well as methods of producing and using same, that fully satisfies the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the invention.

REFERENCES

The following references, to the extent that they provide exemplary procedural or other details supplementary to those set forth herein, are specifically incorporated herein by reference.

Artavanis-Tsakonas S, Rand M D, Lake R J. Notch signaling: cell fate control and signal integration in development. Science 1999; 284:770-6.

Battelli C, Nikopoulos G N, Mitchell J G, Verdi J M. The RNA-binding protein Musashi-1 regulates neural development through the translational repression of p21WAF-1. Mol Cell Neurosci 2006; 31:85-96.

Castedo M, Perfettini J L, Roumier T, Andreau K, Medema R, Kroemer G. Cell death by mitotic catastrophe: a molecular definition. Oncogene 2004; 23:2825-37.

Curry C L, Reed L L, Broude E, Golde T E, Miele L, Foreman K E. Notch inhibition in Kaposi's sarcoma tumor cells leads to mitotic catastrophe through nuclear factor-{kappa}B signaling. Mol Cancer Ther 2007; 6:1983-92.

Hemmati H D, Nakano I, Lazareff J A, Masterman-Smith M, Geschwind D H, Bronner-Fraser M, Kornblum H I. Cancerous stem cells can arise from pediatric brain tumors. Proc Natl Acad Sci USA 2003; 100:15178-83.

Imai T, Tokunaga A, Yoshida T, Hashimoto M, Mikoshiba K, Weinmaster G, Nakafuku M, Okano H. The neural RNA-binding protein Musashi1 translationally regulates mammalian numb gene expression by interacting with its mRNA. Mol Cell Biol 2001; 21:3888-900.

Kanemura Y, Mori K, Sakakibara S, Fujikawa H, Hayashi H, Nakano A, Matsumoto T, Tamura K, Imai T, Ohnishi T, Fushiki S, Nakamura Y, Yamasaki M, Okano H, Arita N. Musashi1, an evolutionarily conserved neural RNA-binding protein, is a versatile marker of human glioma cells in determining their cellular origin, malignancy, and proliferative activity. Differentiation 2001; 68:141-52.

Kawamori T, Uchiya N, Sugimura T, Wakabayashi K. Enhancement of colon carcinogenesis by prostaglandin E2 administration. Carcinogenesis 2003; 24:985-90.

Larcher F, Murillas R, Bolontrade M, Conti C J, Jorcano J L. VEGF/VPF overexpression in skin of transgenic mice induces angiogenesis, vascular hyperpermeability and accelerated tumor development. Oncogene 1998; 17:303-11.

Marshman E, Booth C, Potten C S. The intestinal epithelial stem cell. Bioessays 2002; 24:91-8.

Niculescu A B, 3rd, Chen X, Smeets M, Hengst L, Prives C, Reed S I. Effects of p21(Cip1/Waf1) at both the G1/S and the G2/M cell cycle transitions: pRb is a critical determinant in blocking DNA replication and in preventing endoreduplication. Mol Cell Biol 1998; 18:629-43.

O'Brien C A, Pollett A, Gallinger S, Dick J E. A human colon cancer cell capable of initiating tumour growth in immunodeficient mice. Nature 2007; 445:106-10.

Okano H, Imai T, Okabe M. Musashi: a translational regulator of cell fate. J Cell Sci 2002; 115:1355-9.

Okano H, Kawahara H, Toriya M, Nakao K, Shibata S, Imai T. Function of RNA-binding protein Musashi-1 in stem cells. Exp Cell Res 2005; 306:349-56.

Potten C S, Booth C, Hargreaves D. The small intestine as a model for evaluating adult tissue stem cell drug targets. Cell Prolif 2003; 36:115-29.

Potten C S, Booth C, Tudor G L, Booth D, Brady G, Hurley P, Ashton G, Clarke R, Sakakibara S, Okano H. Identification of a putative intestinal stem cell and early lineage marker; musashi-1. Differentiation 2003; 71:28-41.

Ricci-Vitiani L, Lombardi D G, Pilozzi E, Biffoni M, Todaro M, Peschle C, De Maria R. Identification and expansion of human colon-cancer-initiating cells. Nature 2007; 445:111-5.

Riehl T E, George R J, Sturmoski M A, May R, Dieckgraefe B, Anant S, Houchen C W. Azoxymethane protects intestinal stem cells and reduces crypt epithelial mitosis through a COX-1-dependent mechanism. Am J Physiol Gastrointest Liver Physiol 2006; 291:G1062-70.

Sakakibara S, Imai T, Hamaguchi K, Okabe M, Aruga J, Nakajima K, Yasutomi D, Nagata T, Kurihara Y, Uesugi S, Miyata T, Ogawa M, Mikoshiba K, Okano H. Mouse-Musashi-1, a neural RNA-binding protein highly enriched in the mammalian CNS stem cell. Dev Biol 1996; 176:230-42.

Shao J, Lee S B, Guo H, Evers B M, Sheng H. Prostaglandin E2 stimulates the growth of colon cancer cells via induction of amphiregulin. Cancer Res 2003; 63:5218-23.

Takei Y, Kadomatsu K, Yuzawa Y, Matsuo S, Muramatsu T. A small interfering RNA targeting vascular endothelial growth factor as cancer therapeutics. Cancer Res 2004; 64:3365-70.

Tsao Y P, Huang S J, Chang J L, Hsieh J T, Pong R C, Chen S L. Adenovirus-mediated p21((WAF1/SDII/CIP1)) gene transfer induces apoptosis of human cervical cancer cell lines. J Virol 1999; 73:4983-90.

Ueno M, Katayama K, Yamauchi H, Nakayama H, Doi K. Cell cycle and cell death regulation of neural progenitor cells in the 5-azacytidine (5AzC)-treated developing fetal brain. Exp Neurol 2006; 198:154-66.

Wang D, Wang H, Shi Q, Katkuri S, Walhi W, Desvergne B, Das S K, Dey S K, DuBois R N. Prostaglandin E(2) promotes colorectal adenoma growth via transactivation of the nuclear peroxisome proliferator-activated receptor delta. Cancer Cell 2004; 6:285-95.

Whither RNAi? Nat Cell Biol 2003; 5:489-90.

Yokota N, Mainprize T G, Taylor M D, Kohata T, Loreto M, Ueda S, Dura W, Grajkowska W, Kuo J S, Rutka J T. Identification of differentially expressed and developmentally regulated genes in medulloblastoma using suppression subtraction hybridization. Oncogene 2004; 23:3444-53.

What is claimed is:

1. A short-interfering ribonucleic acid (siRNA) molecule effective at silencing Musashi-1 (Msi-1) expression, wherein said siRNA comprises a sense RNA strand and an antisense RNA strand, wherein the sense and antisense RNA strands form an RNA duplex, and wherein the sense RNA strand comprises a nucleotide sequence identical to a target sequence of about 15 to about 25 contiguous nucleotides in Msi-1 mRNA, wherein the sense RNA strand comprises SEQ ID NO:2.

2. A pharmaceutical composition comprising the siRNA of claim 1.

3. The pharmaceutical composition of claim 2, further comprising at least one additional chemotherapeutic agent.

4. The pharmaceutical composition of claim 2, further comprising a delivery agent.

5. The pharmaceutical composition of claim 4, wherein the delivery agent comprises a liposome.

6. A method of inhibiting expression of Musashi-1 (Msi-1) protein, comprising the steps of:
   providing a cell expressing Msi-1;
   providing a short-interfering ribonucleic acid (siRNA) comprising a sense RNA strand and an antisense RNA strand, wherein the sense and antisense RNA strands form an RNA duplex, wherein the sense RNA strand comprises a nucleotide sequence identical to a target sequence of about 15 to about 25 contiguous nucleotides in Msi-1 mRNA, and wherein the sense RNA strand comprises SEQ ID NO:2; and
   contacting the cell with the siRNA, thereby specifically inhibiting the expression of Msi-1.

7. A method of inhibiting expression of Musashi-1 (Msi-1) protein in a subject, comprising the step of:
   administering to a subject an effective amount of pharmaceutical composition comprising a short-interfering ribonucleic acid (siRNA) comprising a sense RNA strand and an antisense RNA strand, wherein the sense and antisense RNA strands form an RNA duplex, wherein the sense RNA strand comprises a nucleotide sequence identical to a target sequence of about 15 to about 25 contiguous nucleotides in Msi-1 mRNA, and wherein the sense RNA strand comprises SEQ ID NO:2, thereby specifically inhibiting the expression of Msi-1.

8. The method of claim 7, wherein the pharmaceutical composition further comprises a delivery agent.

9. The method of claim 8, wherein the delivery agent comprises a liposome.

10. A method of inhibiting tumor growth, comprising the steps of:
    providing a short-interfering ribonucleic acid (siRNA) comprising a sense RNA strand and an antisense RNA strand, wherein the sense and antisense RNA strands form an RNA duplex, wherein the sense RNA strand comprises a nucleotide sequence identical to a target sequence of about 15 to about 25 contiguous nucleotides in Msi-1 mRNA, and wherein the sense RNA strand comprises SEQ ID NO:2; and
    contacting the tumor with the siRNA, thereby specifically inhibiting the expression of Msi-1 in the tumor and thus inhibiting growth of the tumor.

11. A method of inhibiting tumor growth in a subject, comprising the steps of:
    providing a pharmaceutical composition comprising a short-interfering ribonucleic acid (siRNA), the siRNA comprising a sense RNA strand and an antisense RNA strand, wherein the sense and antisense RNA strands form an RNA duplex, and wherein the sense RNA strand comprises a nucleotide sequence identical to a target sequence of about 15 to about 25 contiguous nucleotides in Msi-1 mRNA, and wherein the sense RNA strand comprises SEQ ID NO:2; and
    administering an effective amount of the pharmaceutical composition to the subject, thereby specifically inhibiting the expression of Msi-1 in the tumor and thus inhibiting growth of the tumor.

* * * * *

UNITED STATES PATENT AND TRADEMARK OFFICE
CERTIFICATE OF CORRECTION

| | | |
|---|---|---|
| PATENT NO. | : 7,956,044 B1 | Page 1 of 1 |
| APPLICATION NO. | : 12/384387 | |
| DATED | : June 7, 2011 | |
| INVENTOR(S) | : Houchen et al. | |

It is certified that error appears in the above-identified patent and that said Letters Patent is hereby corrected as shown below:

In the Specification:

Column 16, line 34: Before "phase" delete "GSM" and replace with -- $G_2/M$ --.

Column 16, line 42: Delete "GSM" and replace with -- $G_2/M$ --.

Signed and Sealed this
Sixteenth Day of August, 2011

David J. Kappos
*Director of the United States Patent and Trademark Office*